US009309284B2

(12) United States Patent
Chang et al.

(10) Patent No.: US 9,309,284 B2
(45) Date of Patent: Apr. 12, 2016

(54) MACROCYCLIC AND PEPTIDOMIMETIC COMPOUNDS AS BROAD-SPECTRUM ANTIVIRALS AGAINST 3C OR 3C-LIKE PROTEASES OF PICORNAVIRUSES, CALICIVIRUSES AND CORONAVIRUSES

(71) Applicants: Kansas State University Research Foundation, Manhattan, KS (US); Wichita State University, Wichita, KS (US)

(72) Inventors: Kyeong-Ok Chang, Manhattan, KS (US); Yunjeong Kim, Manhattan, KS (US); William C. Groutas, Wichita, KS (US)

(73) Assignees: Kansas State University Reasearch Foundation, Manhattan, KS (US); Wichita State University, Wichita, KS (US)

( * ) Notice: Subject to any disclaimer, the term of this patent is extended or adjusted under 35 U.S.C. 154(b) by 0 days.

(21) Appl. No.: 14/398,290

(22) PCT Filed: May 2, 2013

(86) PCT No.: PCT/US2013/039314
§ 371 (c)(1),
(2) Date: Oct. 31, 2014

(87) PCT Pub. No.: WO2013/166319
PCT Pub. Date: Nov. 7, 2013

(65) Prior Publication Data
US 2015/0133368 A1 May 14, 2015

Related U.S. Application Data

(63) Continuation-in-part of application No. PCT/US2012/057609, filed on Sep. 27, 2012.

(60) Provisional application No. 61/641,552, filed on May 2, 2012.

(51) Int. Cl.
| | |
|---|---|
| *A61K 38/07* | (2006.01) |
| *C07K 5/103* | (2006.01) |
| *A61K 31/4192* | (2006.01) |
| *A61K 45/06* | (2006.01) |
| *A61K 31/454* | (2006.01) |
| *A61K 31/675* | (2006.01) |
| *C07K 5/097* | (2006.01) |
| *C07K 5/078* | (2006.01) |
| *A61K 38/05* | (2006.01) |
| *C07K 5/062* | (2006.01) |
| *A61K 38/00* | (2006.01) |

(52) U.S. Cl.
CPC ............ *C07K 5/1008* (2013.01); *A61K 31/4192* (2013.01); *A61K 31/454* (2013.01); *A61K 31/675* (2013.01); *A61K 38/05* (2013.01); *A61K 38/07* (2013.01); *A61K 45/06* (2013.01); *C07K 5/06026* (2013.01); *C07K 5/06139* (2013.01); *C07K 5/0821* (2013.01); *A61K 38/00* (2013.01); *A61K 38/005* (2013.01)

(58) Field of Classification Search
None
See application file for complete search history.

(56) References Cited

U.S. PATENT DOCUMENTS

| | | | |
|---|---|---|---|
| 5,856,530 | A | 1/1999 | Webber et al. |
| 6,649,639 | B2 | 11/2003 | Dragovich et al. |
| 7,462,594 | B2 | 12/2008 | Yang et al. |
| 2006/0014821 | A1 | 1/2006 | He et al. |

FOREIGN PATENT DOCUMENTS

| | | |
|---|---|---|
| WO | 97/43305 | 11/1997 |
| WO | 9931122 | 6/1999 |
| WO | 0110894 | 2/2001 |
| WO | 0218369 | 3/2002 |
| WO | 2006061714 | 6/2006 |
| WO | 2011079076 | 6/2011 |

OTHER PUBLICATIONS

Tiew, Kok-Chuan et al, "Design, synthesis, and evaluation of inhibitors of norwalk virus 3c protease." Bioorg. Med. Chem. Lett. (2011) 21 p. 5315-5319).*
The International Search Report and Written Opinion dated Aug. 28, 2013, in the corresponding PCT application No. PCT/US2013/039314, filed May 2, 2013.
The International Search Report and Written Opinion dated Mar. 15, 2013, in the related PCT application No. PCT/US2012/057609, filed Sep. 27, 2012.

* cited by examiner

*Primary Examiner* — Maury Audet
*Assistant Examiner* — Fred Reynolds
(74) *Attorney, Agent, or Firm* — Hovey Williams LLP

(57) ABSTRACT

Antiviral protease inhibitors, including macrocylic transition state inhibitors and peptidomimetics are disclosed, along with related antiviral compounds, and methods of using the same to treat or prevent viral infection and disease. The compounds possess broad-spectrum activity against viruses that belong to the picornavirus-like supercluster, which include important human and animal pathogens including noroviruses, sapoviruses, enteroviruses, poliovirus, foot-and-mouth disease virus, hepatitis A virus, human rhinovirus (cause of common cold), human coronavirus (another cause of common cold), transmissible gastroenteritis virus, murine hepatitis virus, feline infectious peritonitis virus, and severe acute respiratory syndrome coronavirus.

26 Claims, 10 Drawing Sheets

$^i$DBU/Cu(I)Br/DCM; $^j$2M LiBH4/THF; $^k$Dess-Martin periodinane/DCM (I)

[a]HATU/DMAP/TEA/DMF then (L) Cyclohexylalanine-OMe(HCl); [b]LiOH(aq)/THF; [c]EDCI/HOBt/DIEA/DMF then (L) Glutamine surrogate-OMe(HCl); [d]2M LiBH$_4$/THF; [e]Dess-Martin periodinane/DCM

MACROCYCLIC AND PEPTIDOMIMETIC COMPOUNDS AS BROAD-SPECTRUM ANTIVIRALS AGAINST 3C OR 3C-LIKE PROTEASES OF PICORNAVIRUSES, CALICIVIRUSES AND CORONAVIRUSES

CROSS-REFERENCE TO RELATED APPLICATIONS

The present application is the National Stage of PCT/US2013/039314, filed May 2, 2013, which claims the priority benefit of U.S. Provisional patent application Ser. No. 61/641,552, filed May 2, 2012, entitled Novel Broad-Spectrum Antivirals against 3C or 3C—like Proteases of Picornavirus-like Supercluster: Picornaviruses, Noroviruses and Coronaviruses, and International Patent Application No. PCT/US2012/057609, filed Sep. 27, 2012, entitled Broad -Spectrum Antivirals against 3C or 3C—like proteases of Picornavirus-like Supercluster: Picornaviruses, Caliciviruses and Coronaviruses, all of which are incorporated by reference in their entireties herein.

STATEMENT REGARDING FEDERALLY-FUNDED RESEARCH

This invention was made with U.S. Government support under grant number U01 A1081891 awarded by the National Institute of Health. The U.S. Government has certain rights in the invention.

SEQUENCE LISTING

The nucleic and amino acid sequences listed in the accompanying Sequence Listing are presented in accordance with 37 C.F.R. 1.822. The Sequence Listing is submitted as an ASCII computer readable text file, created on May 1, 2013 as 4 KB, which is incorporated by reference herein.

BACKGROUND OF THE INVENTION

1. Field of the Invention

The present invention relates to broad-spectrum antiviral compounds targeting the 3C or 3C-like ("3CL") proteases of the picornavirus-like supercluster.

2. Description of Related Art

Many viruses encode polyproteins with proteases which catalyze their subsequent cleavage to the mature functional proteins and are essential for viral replication. Previous attempts have been made to inhibit viral activity by targeting such proteases. However, most protease inhibitors have a short range of specificity that is genus-, species-, or even strain-specific due to structural variations in the viral proteases. Thus, broad spectrum antivirals are rare and have proven elusive to researchers.

Caliciviruses, such as the norovirus and sapovirus genera, cause acute gastroenteritis in humans and animals. Noroviruses are the most common cause of acute viral gastroenteritis in the United States and worldwide, accounting for ~21 million cases of gastroenteritis in the U.S. alone. Noroviruses are highly contagious and cause outbreaks in enclosed settings such as navy and cruise ships, army barracks, schools, and hospitals. Noroviruses are very stable in the environment and refractory to many common disinfectants, with only a few virions required to initiate virus infection and shedding which could be a source for further contamination. Norovirus infection constitutes an important public health problem, as well as a potential bioterrorism threat, and is classified as a Category B priority pathogen by NIAID and a class B bioterrorism agent by the CDC. The problem is further compounded by the absence of specific norovirus antiviral therapeutics or vaccines. Vaccine development for human noroviruses faces additional obstacles because norovirus strain diversity is high, and immunity to one strain does not necessarily provide protection from infection with other strains. Furthermore, repeat infections with the same norovirus strain in adults indicate that long-term immunity may be absent. Thus, there is currently an urgent and unmet need for the development of antiviral therapeutics for the treatment and prevention of norovirus infection. There is also a need for antiviral therapies for treating and preventing other viruses, such as medically important coronaviruses and picornaviruses, including but not limited to severe acute respiratory syndrome coronavirus (SARS-CoV), feline infectious peritonitis virus (FIPV), human rhinovirus (HRV), coxsackievirus (CV), and enteroviruses (EV).

SUMMARY OF THE INVENTION

In one aspect, an antiviral compound comprising:

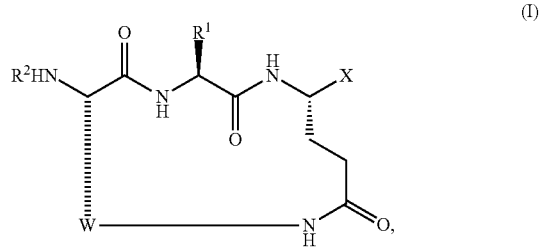

(I)

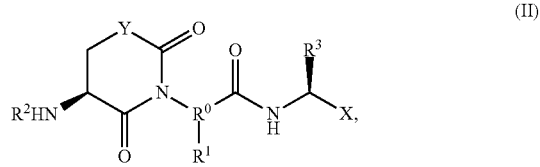

(II)

or the pharmaceutically-acceptable salts thereof is provided, where:

each X is selected from the group consisting of aldehydes; bisulfite salts; ketoamides; α-hydroxyphosphonates; sulfonamides; and ketones;

each $R^0$ is —CH— or —N—;

each $R^1$ is a natural or non-naturally occurring amino acid side chain such as branched or unbranched alkyl, cycloalkyl, aryl, arylalkyl, or a combination thereof;

each $R^2$ is selected from the group consisting of —C(O)$OR^8$, where $R^8$ is alkyl, cycloalkyl, or substituted or unsubstituted: aryl, arylalkyl, aryloxy, heteroaryloxy, arylalkoxy, heteroarylalkoxy, or aromatic heterocyclic ring; —C(O)NH$R^9$, where $R^9$ is alkyl, cycloalkyl, or substituted or unsubstituted: aryl, arylalkyl, aryloxy, heteroaryloxy, arylalkoxy, heteroarylalkoxy, or aromatic heterocyclic ring; and —SO$_2R^{10}$, where $R^{10}$ is alkyl, cycloalkyl, or substituted or unsubstituted: aryl, arylalkyl, aryloxy, heteroaryloxy, arylalkoxy, heteroarylalkoxy, or aromatic heterocyclic ring;

each $R^3$ is selected from the group consisting of

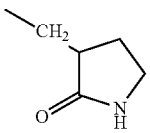

and —$(CH_2)_2C(O)NR^{14}R^{15}$, where $R^{14}$ is alkyl, cycloalkyl, or arylalkyl, and $R^{15}$ is H or alkyl, or $R^{14}$ and $R^{15}$ are tethered together to form a cyclic amine;

each W is selected from the group consisting of —$(CH_2)_x$—, where x is 4 to 10 (preferably 8); —$CH_2Q(CH_2)_z$—, where Q is S or O, and z is 4 to 8; —$(CH_2)_mC(O)NR^{11}(CH_2)_p$—, where $R^{11}$ is H or methyl, m is 1 to 2, and p is 3 to 6; —$CH_2Im(CH_2)_r$—, where Im is imidazole and r is 3 to 6; —$(CH_2)_sTr(CH_2)_s$—, where Tr is a 1,4- or 1,5-substituted triazole and each s is 1 to 4; and —$(CH_2)_tR^{12}(CH_2)_t$—, where $R^{12}$ is a phenyl or heterocyclic ring, and each t is 1 to 4; and each Y is —$CH_2$— or $NR^{13}$, where $R^{13}$ is H, alkyl, cycloalkyl, or arylalkyl.

A method of treating or preventing viral infection in a subject from one or more viruses selected from the group consisting of caliciviruses, picornaviruses, and/or coronaviruses is also provided. The method comprises administering to said subject a therapeutically-effective amount of a first antiviral compound according to the various embodiments described herein.

A broad spectrum antiviral composition is also disclosed. The composition comprises a first antiviral compound according to the various embodiments described herein dispersed in a pharmaceutically-acceptable carrier.

A kit is also provided herein. The kit comprises: an antiviral compound according to the various embodiments described herein; and instructions for administering the compound to a subject in need thereof.

A method of preventing or inhibiting replication of a virus in a cell is also disclosed. The method comprises contacting the cell with a compound according to the various embodiments described herein, wherein the virus is selected from the group consisting of caliciviruses, picornaviruses, coronaviruses, and combinations thereof.

The invention is also concerned with the use of a compound according to the various embodiments described herein to prepare a therapeutic or prophylactic medicament for the treatment or prevention of a viral infection from caliciviruses, picornaviruses, and/or coronaviruses in a subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
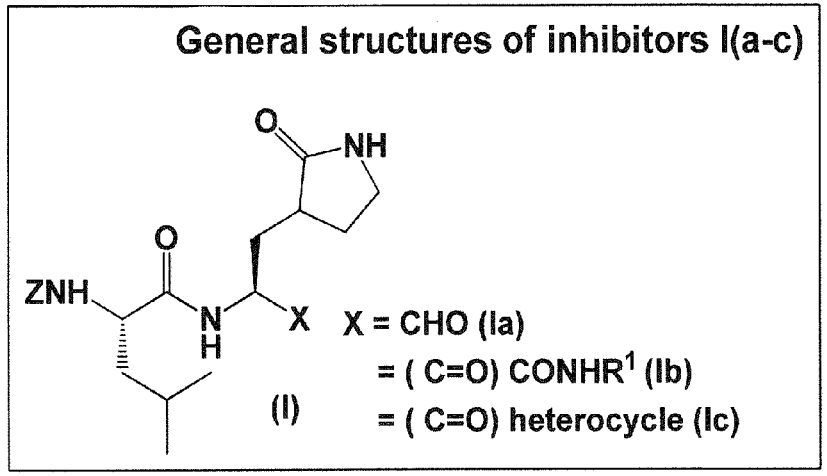
FIG. 1 shows the general structure of previously-synthesized protease inhibitors from Example 1.
Figure 2:
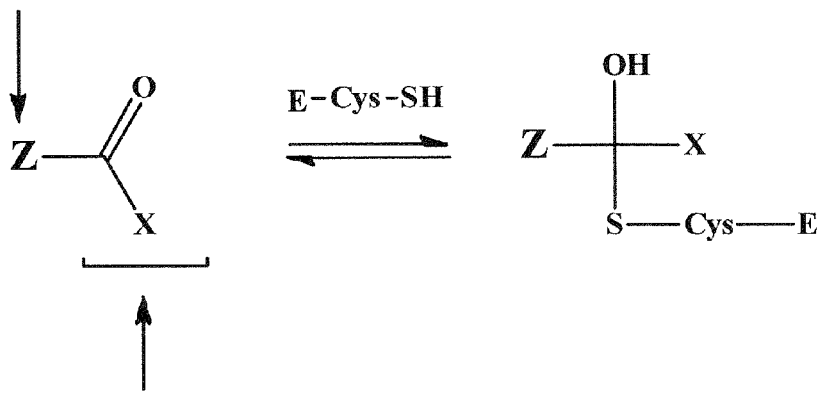
FIG. 2 is a general illustration of the interaction between a cysteine protease and a transition state inhibitor.
Figure 3:
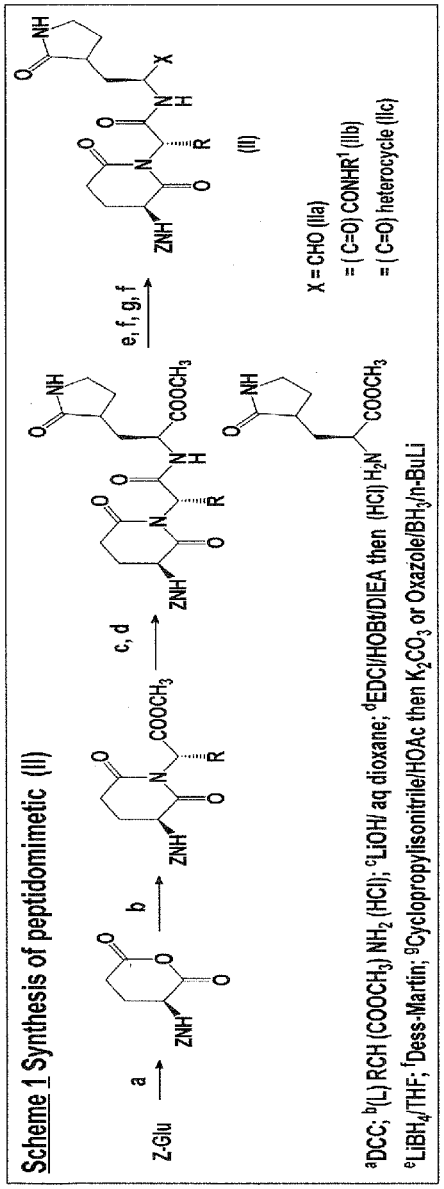
FIG. 3 shows the reaction schemes for synthesizing various peptidomimetic inhibitors described in Example 1.
Figure 3:
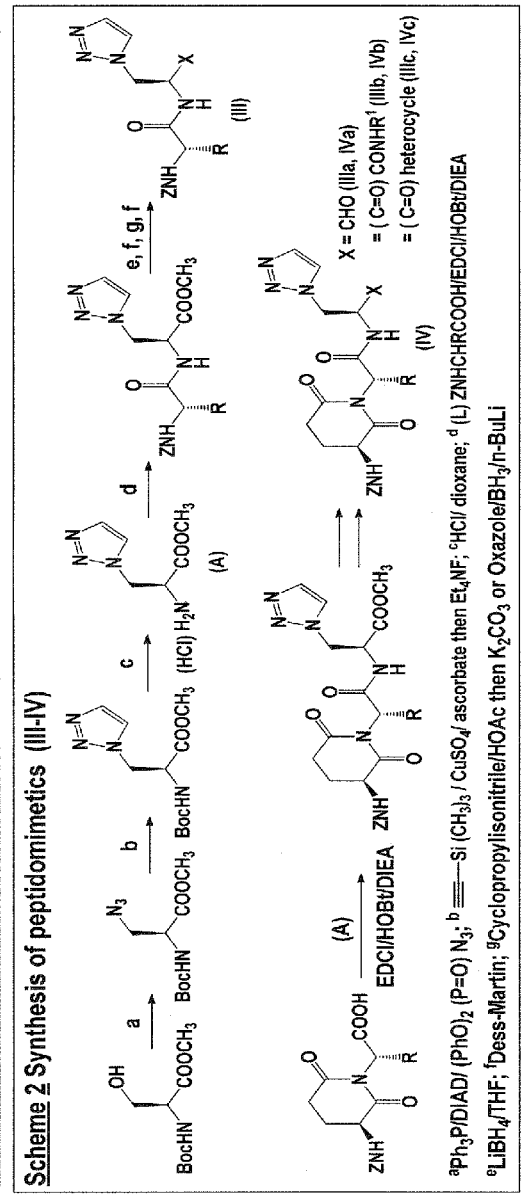
Figure 4:
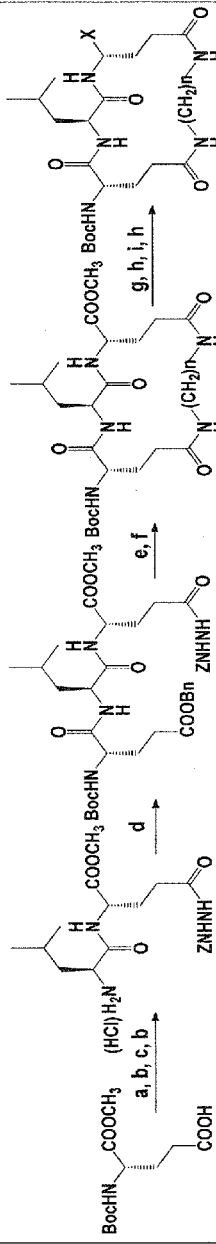
FIG. 4 shows the reaction schemes for synthesizing various macrocylic inhibitors described in Example 1.
Figure 4:
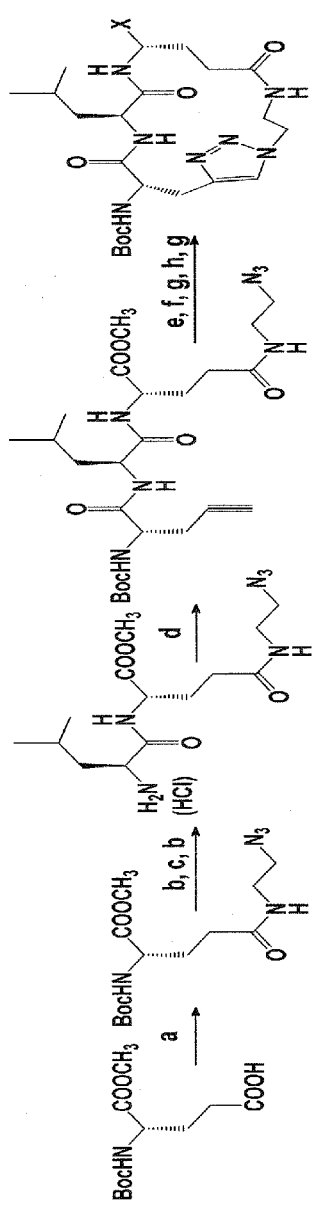
Figure 4:
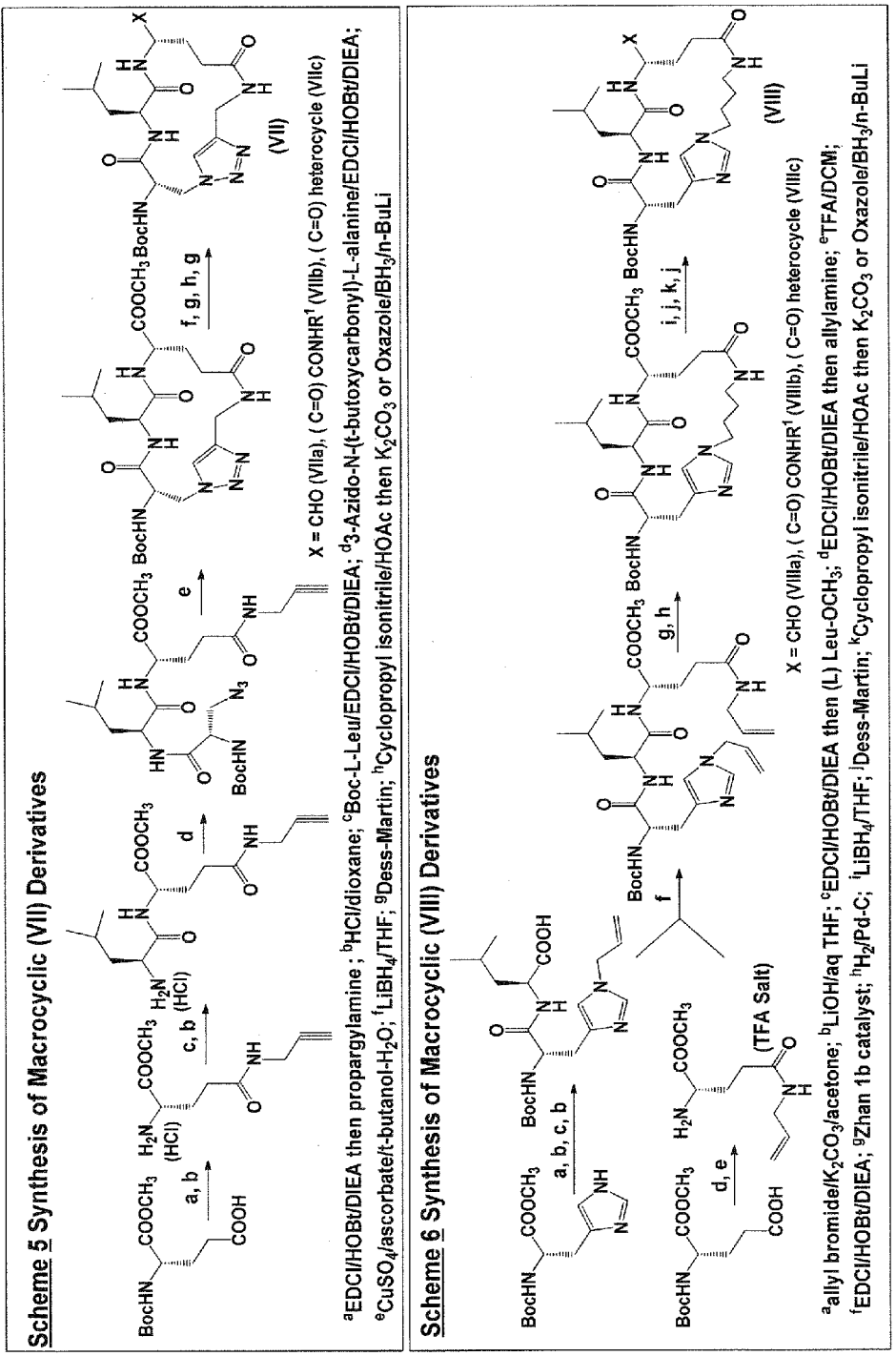

Among positive sense RNA viruses, genetic analysis has demonstrated that certain viruses can be classified as members of the picornavirus-like "supercluster," which includes picornaviruses, caliciviruses, and coronaviruses. A common feature of these viruses is that they possess a viral 3C or 3CL protease which is responsible for most cleavages of the corresponding viral polyprotein. These 3C and 3CL proteases share some common characteristics, including a typical chymotrypsin-like fold and a catalytic triad (or dyad) with Cys-His-Glu (or Asp) on the protease, and a preference for a Glu or Gln residue at the P1 position on the substrate. High resolution 3D structures of these proteases have confirmed the conservation of active sites with the catalytic triad or dyad and substrate binding pockets. Viruses in the picornavirus-like supercluster include important human and animal pathogens. For example, caliciviruses include human sapovirus, human noroviruses (such as Norwalk virus [NV] and MD145), feline calicivirus, murine norovirus (MNV), vesicular exanthema of swine virus, and rabbit hemorrhagic disease virus. Picornaviruses include human EV (such as EV 71), poliovirus, CV, foot-and-mouth disease virus (FMDV), hepatitis A virus (HAV), porcine teschovirus, and HRV (cause of common cold). Coronaviruses include human coronavirus (cause of common cold such as 229E strain), transmissible gastroenteritis virus (TGEV), murine hepatitis virus (MHV), bovine coronavirus (BCV), FIPV, and SARS-CoV.

A series of novel macrocyclic transition state inhibitors and peptidomimetics have been synthesized and demonstrated to possess broad-spectrum activity against viruses that belong to the picornavirus-like supercluster. Members of this series of compounds are highly effective as antiviral therapeutics targeting a specific virus and, more importantly, can also be used as broad-spectrum antivirals targeting multiple viruses. The wide applicability of the latter constitutes a significant advance in antiviral research and public health.

Embodiments described herein include antiviral compounds having broad-spectrum (multivalent) activity against viruses that belong to the picornavirus-like supercluster, including caliciviruses, picornaviruses, and coronaviruses. The compounds are macrocyclic antivirals and peptidomimetics, which will be highly effective against such viruses with low cytotoxicity. These compounds have broad-spectrum therapeutic value against multiple viruses of the picornavirus-like supercluster, which includes important classical and emerging animal and human pathogens. The compounds effectively target and inhibit viral 3C or 3CL protease activity across multiple virus species, strains, and subtypes, thereby preventing formation of the mature virus and inhibiting virus replication in the host cell. The compounds have a therapeutic index (ratio of lethal or toxic dose to therapeutic dose) of greater than about 50:1, indicating the relative safety of such compounds for use in human and veterinary applications.

In some embodiments, antiviral compounds comprising (consisting essentially or even consisting of) formula (I), or the pharmaceutically-acceptable salts thereof, are provided:

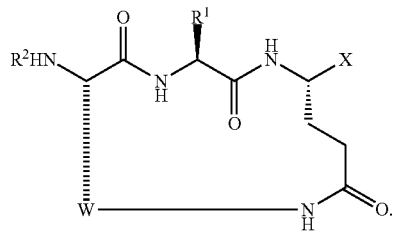
(I)

In the foregoing structure (I), each X is selected from the group consisting of: aldehydes (such as —CHO); bisulfite salts (e.g., —CH(OH)SO$_3^-$Na$^+$); ketoamides (such as —C(O)C(O)NHR$^4$, where R$^4$ is a branched or unbranched alkyl (e.g., methyl, ethyl, butyl, isobutyl), cycloalkyl, or arylalkyl); α-hydroxyphosphonates (such as —CH(OH)(P=O)(OR$^5$)$_2$, where R$^5$ is —H, a substituted or unsubstituted alkyl (e.g., methyl, ethyl, butyl, trifluoroethyl), aryl, or arylalkyl (e.g., benzyl)); sulfonamides (such as —C(O)NHSO$_2$R$^6$, where R$^6$ is an alkyl, cycloalkyl, substituted or unsubstituted aryl, or arylalkyl); and ketones (such as —C(O)R$^7$, where R$^7$ is CF$_3$ or a heterocyclic ring (e.g., oxazole, benzoxazole, thiazole, benzothiazole, or oxadiazole)).

Each R$^1$ in the structure (I) above is a natural or non-naturally occurring amino acid side chain, such as branched or unbranched alkyl (e.g., methyl, ethyl, butyl, isobutyl), cycloalkyl (e.g. cyclohexylmethyl), aryl (e.g., phenyl), arylalkyl (e.g. benzyl or group where the aryl is naphthyl), or a combination thereof.

In the structure (I) above, each R$^2$ is selected from the group consisting of:—C(O)OR$^8$, where R$^8$ is alkyl, cycloalkyl, or substituted or unsubstituted: aryl, arylalkyl, aryloxy, heteroaryloxy, arylalkoxy, heteroarylalkoxy, or aromatic heterocyclic ring; —C(O)NHR$^9$, where R$^9$ is alkyl, cycloalkyl, or substituted or unsubstituted: aryl, arylalkyl, aryloxy, heteroaryloxy, arylalkoxy, heteroarylalkoxy, or aromatic heterocyclic ring; and —SO$_2$R$^{10}$, where R$^{10}$ is alkyl, cycloalkyl, or substituted or unsubstituted: aryl, arylalkyl, aryloxy, heteroaryloxy, arylalkoxy, heteroarylalkoxy, or aromatic heterocyclic ring. For example, suitable aryl and arylalkyl substitutions include one or more halogens, cyano groups, thioethers, sulfones, aminos, and hydroxyl groups, at the o-, m-, and/or p-positions. Aromatic heterocyclic rings can be substituted with N, O, S, or NH. In one or more embodiments, suitable aromatic heterocyclic rings include furans, pyrroles, thiophenes, imidazoles, oxazoles, thiazoles, and the like.

Each W in the structure (I) above is selected from the group consisting of: —(CH$_2$)$_x$—, where x is 4 to 10 (preferably 8); —CH$_2$Q(CH$_2$)$_z$—, where Q is S or O, and z is 4 to 8; —(CH$_2$)$_m$C(O)NR$^{11}$(CH$_2$)$_p$—, where R$^{11}$ is H or methyl, m is 1 to 2, and p is 3 to 6; —CH$_2$Im(CH$_2$)$_r$—, where Im is imidazole and r is 3 to 6; —(CH$_2$)$_s$Tr(CH$_2$)$_s$—, where Tr is a 1,4- or 1,5-substituted triazole and each s is 1 to 4; and —(CH$_2$)$_t$R$^{12}$(CH$_2$)$_t$—, where R$^{12}$ is a phenyl or heterocyclic ring (e.g., isoxazole, oxadiazole, etc.), and each t is 1 to 4.

More preferably, in macrocyclic antivirals according to formula (I) above, each R$^1$ is isobutyl, cyclohexylalkyl, or benzyl; and each R$^2$ is —C(O)OR$^8$, where R$^8$ is alkyl, cycloalkyl, substituted or unsubstituted aryl, arylalkyl, or an aromatic heterocyclic ring; —C(O)NHR$^9$, where R$^9$ is alkyl, cycloalkyl, substituted or unsubstituted aryl, arylalkyl, or an aromatic heterocyclic ring; or —SO$_2$R$^{10}$, where R$^{10}$ is alkyl, cycloalkyl, substituted or unsubstituted aryl, arylalkyl, or an aromatic heterocyclic ring. In one or more embodiments, each R$^2$ is a substituted or unsubstituted carboxybenzyl group (i.e., —C(O)OR$^8$, where R$^8$ is a substituted or unsubstituted benzyl).

In some embodiments, antiviral compounds comprising (consisting essentially or even consisting of) formula (II), or the pharmaceutically-acceptable salts thereof, are provided:

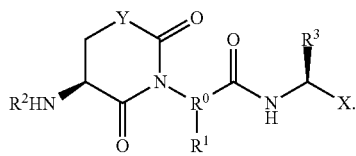
(II)

Each X, R$^1$, and R$^2$ in structure (II) above is individually defined according to the definitions given for formula (I) above. Each Y in structure (II) is —CH$_2$— or NR$^{13}$, where R$^{13}$ is H, alkyl, cycloalkyl, or arylalkyl; each R$^0$ is —CH— or —N—; and each R$^3$ is selected from the group consisting of

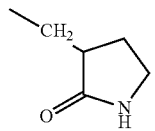

and
—CH$_2$ where R$^{14}$ is alkyl, cycloalkyl, or arylalkyl, and R$^{15}$ is H or alkyl, or R$^{14}$ and R$^{15}$ are tethered together to form a cyclic amine (preferably C$_3$-C$_7$).

More preferably, in peptidomimetics according to formula (II) above, each R$^1$ is preferably alkyl, cycloalkyl, or arylalkyl; and each R$^2$ is preferably —C(O)OR$^8$, where R$^8$ is alkyl, cycloalkyl, substituted or unsubstituted aryl, arylalkyl, or heterocylic aromatic ring; —C(O)NHR$^9$, where R$^9$ is alkyl, cycloalkyl, substituted or unsubstituted aryl, arylalkyl, or heterocylic aromatic ring; or —SO$_2$R$^{10}$, where R$^{10}$ is alkyl, cycloalkyl, substituted and unsubstituted aryl, arylalkyl, or heterocylic aromatic ring. In one or more embodiments, each R$^2$ is a carboxybenzyl group.

The term "pharmaceutically-acceptable salt," as used herein, refers to an acid or base salt of a compound of the invention, which salt possesses the desired antiviral activity and is neither biologically nor otherwise undesirable. Combinations of one or more of the foregoing compounds can also be used in the invention.

In one or more embodiments, the antiviral compounds are macrocycles and/or peptidomimetics selected from the group consisting of:

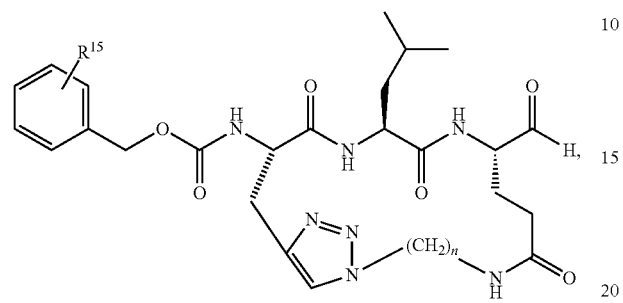

n = 1, 2, 3, or 4
R$^{15}$ = hydrogen, halogen, cyano, methoxy, thioether, sulfone, amino, or hydroxyl

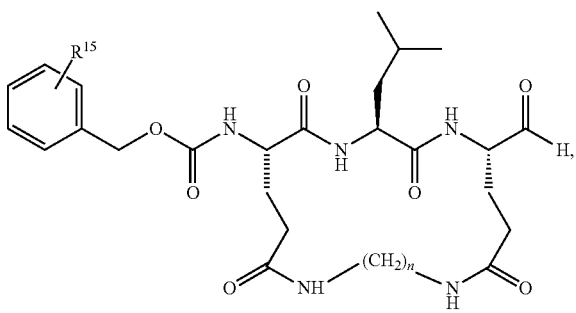

n = 1, 2, 3, or 4
R$^{15}$ = hydrogen, halogen, cyano, methoxy, thioether, sulfone, amino, or hydroxyl

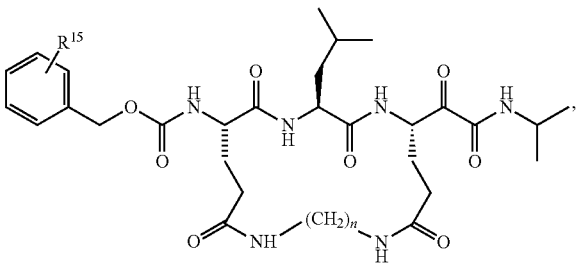

n = 1, 2, 3, or 4
R$^{15}$ = hydrogen, halogen, cyano, methoxy, thioether, sulfone, amino, or hydroxyl Q = O or S
n = 1, 2, 3, or 4
R$^{15}$ = hydrogen, halogen, cyano, methoxy, thioether, sulfone, amino, or hydroxyl

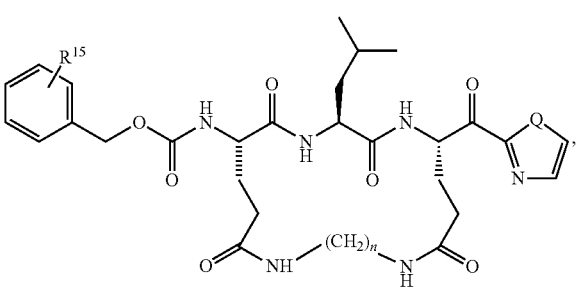

Q = O or S
n = 1, 2, 3, or 4
R$^{15}$ = hydrogen, halogen, cyano, methoxy, thioether, sulfone, amino, or hydroxyl

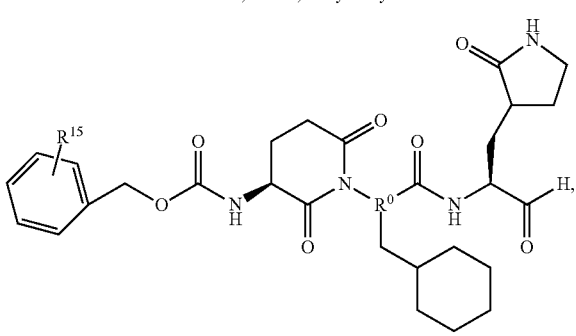

n = 1, 2, 3, or 4
R$^{15}$ = hydrogen, halogen, cyano, methoxy, thioether, sulfone, amino, or hydroxyl R$^0$ = CH or N
R$^{15}$ = hydrogen, halogen, cyano, methoxy, thioether, sulfone, amino, or hydroxyl

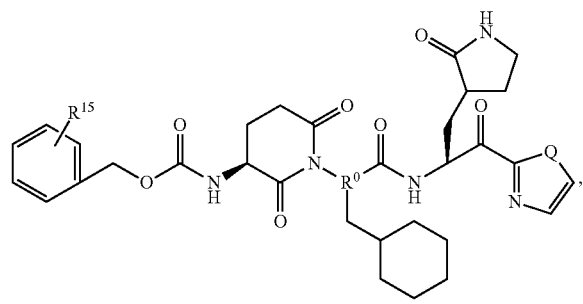

Q = O or S
R⁰ = CH or N
$R^{15}$ = hydrogen, halogen, cyano, methoxy, thioether, sulfone, amino, or hydroxyl.

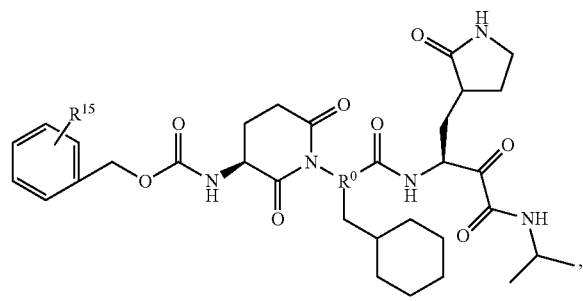

R⁰ = CH or N
$R^{15}$ = hydrogen, halogen, cyano, methoxy, thioether, sulfone, amino, or hydroxyl

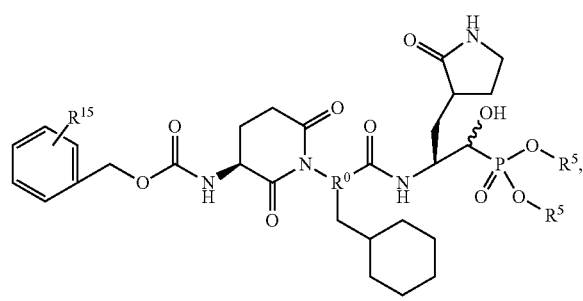

R⁰ = CH or N
each $R^5$ = H, methyl, ethyl, n-butyl, trifluoroethyl, or benzyl
$R^{15}$ = hydrogen, halogen, cyano, methoxy, thioether, sulfone, amino, or hydroxyl

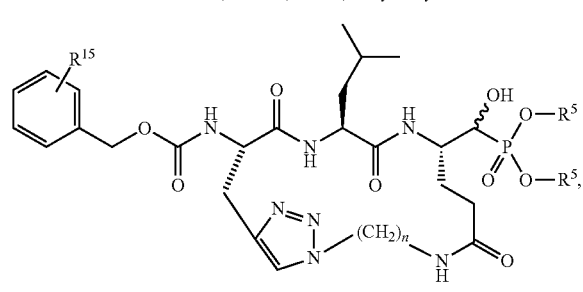

n = 1, 2, 3, or 4
each $R^5$ = H, methyl, ethyl, n-butyl, trifluoroethyl, or benzyl
$R^{15}$ = hydrogen, halogen, cyano, methoxy, thioether, sulfone, amino, or hydroxyl

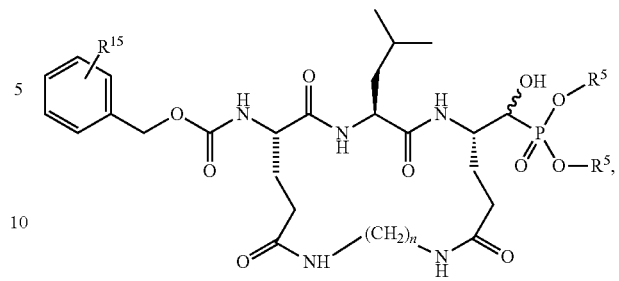

n = 1, 2, 3, or 4
each $R^5$ = H, methyl, ethyl, n-butyl, trifluoroethyl, or benzyl
$R^{15}$ = hydrogen, halogen, cyano, methoxy, thioether, sulfone, amino, or hydroxyl and the pharmaceutically-acceptable salts thereof. Combinations of one or more of the foregoing compounds can also be used in the invention.

In one or more embodiments, the antiviral compounds are macrocycles and/or peptidomimetics selected from the group consisting of:

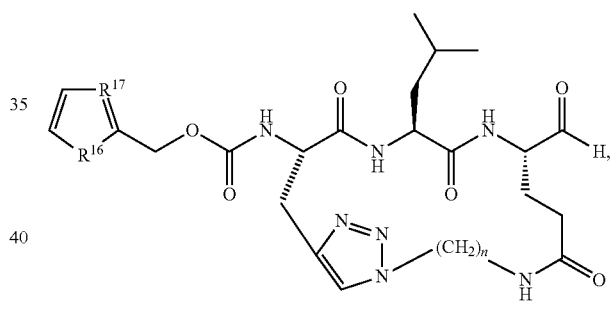

n = 1, 2, 3, or 4
$R^{16}$ = NH, O, or S
$R^{17}$ = CH or N

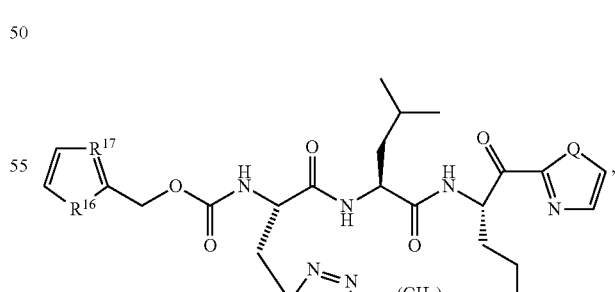

Q = O or S
n = 1, 2, 3, or 4
$R^{16}$ = NH, O, or S
$R^{17}$ = CH or N

11
-continued
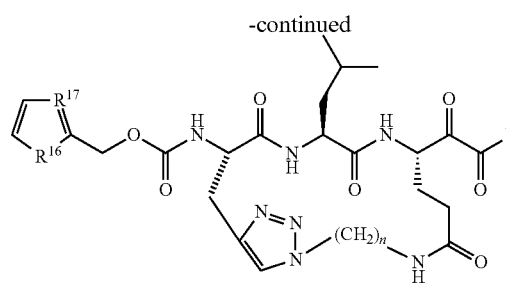
n = 1, 2, 3, or 4
R^16 = NH, O, or S
R^17 = CH or N
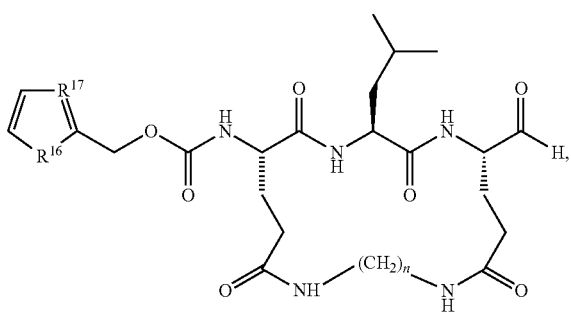
n = 1, 2, 3, or 4
R^16 = NH, O, or S
R^17 = CH or N
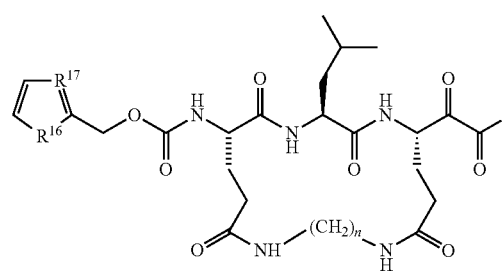
n = 1, 2, 3, or 4
R^16 = NH, O, or S
R^17 = CH or N
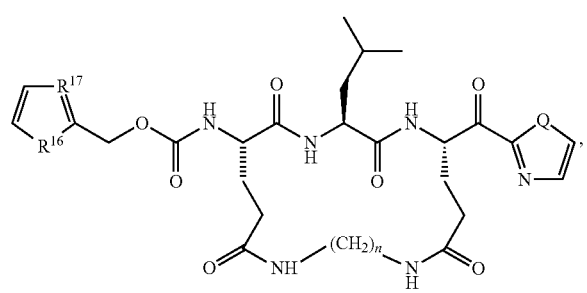
Q = O or S
n = 1, 2, 3, or 4
R^16 = NH, O, or S
R^17 = CH or N
12
-continued
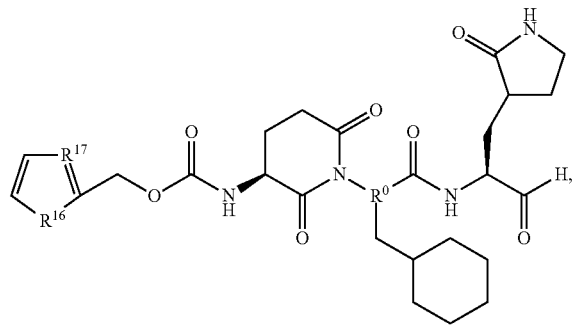
R^0 = CH or N
R^16 = NH, O, or S
R^17 = CH or N
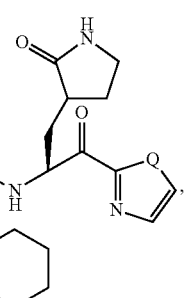
Q = O or S
R^0 = CH or N
R^16 = NH, O, or S
R^17 = CH or N
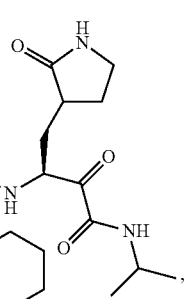
R^0 = CH or N
R^16 = NH, O, or S
R^17 = CH or N
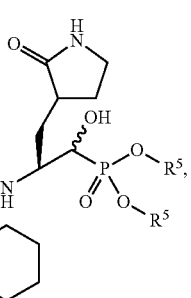
R^0 = CH or N
R^16 = NH, O, or S
R^17 = CH or N
each R^5 = H, methyl, ethyl, n-butyl,
trifluoroethyl, or benzyl

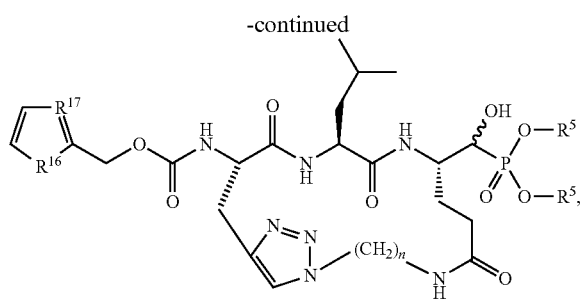

n = 1, 2, 3, or 4
$R^{16}$ = NH, O, or S
$R^{17}$ = CH or N
each $R^5$ = H, methyl, ethyl,
n-butyl, trifluoroethyl, or benzyl

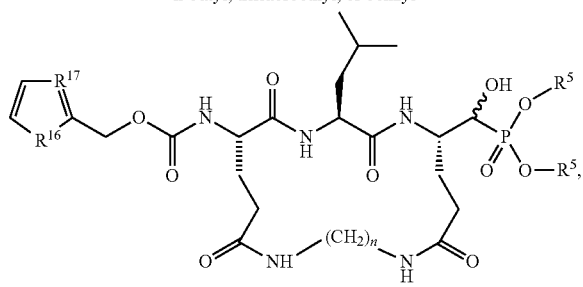

n = 1, 2, 3, or 4
each $R^5$ = H, methyl, ethyl,
n-butyl, trifluoroethyl, or benzyl
$R^{16}$ = NH, O, or S
$R^{17}$ = CH or N and the pharmaceutically-acceptable salts thereof. Combinations of one or more of the foregoing compounds can also be used in the invention.

Prophylactic and/or therapeutic compositions with specific or broad-spectrum antiviral activities are also disclosed. The compositions comprise an antiviral compound described herein dispersed in a pharmaceutically-acceptable carrier. The term carrier is used herein to refer to diluents, excipients, vehicles, and the like, in which the antiviral may be dispersed for administration. Suitable carriers will be pharmaceutically acceptable. As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained. A pharmaceutically-acceptable carrier would naturally be selected to minimize any degradation of the compound or other agents and to minimize any adverse side effects in the subject, as would be well known to one of skill in the art. Pharmaceutically-acceptable ingredients include those acceptable for veterinary use as well as human pharmaceutical use, and will depend on the route of administration. For example, compositions suitable for administration via injection are typically solutions in sterile isotonic aqueous buffer. Exemplary carriers include aqueous solutions such as normal (n.) saline (~0.9% NaCl), phosphate buffered saline (PBS), sterile water/distilled autoclaved water (DAW), various oil-in-water or water-in-oil emulsions, as well as dimethyl sulfoxide (DMSO) or other acceptable vehicles, and the like.

The composition can comprise a therapeutically effective amount of the compound(s) dispersed in the carrier. As used herein, a "therapeutically effective" amount refers to the amount that will elicit the biological or medical response of a tissue, system, or subject that is being sought by a researcher or clinician, and in particular elicit some desired therapeutic or prophylactic effect as against the viral infection by preventing and/or inhibiting 3C or 3CL protease activity and/or viral replication. One of skill in the art recognizes that an amount may be considered therapeutically "effective" even if the condition is not totally eradicated or prevented, but it or its symptoms and/or effects are improved or alleviated partially in the subject. In some embodiments, the composition will comprise from about 5% to about 95% by weight of an antiviral compound described herein, and preferably from about 30% to about 90% by weight of the antiviral compound, based upon the total weight of the composition taken as 100% by weight. In some embodiments, combinations of more than one type of the described antiviral compounds can be included in the composition, in which case the total levels of all such compounds will preferably fall within the ranges described above.

Other ingredients may be included in the composition, such as other active agents, preservatives, buffering agents, salts, or other pharmaceutically-acceptable ingredients. The active agents that could be included in the composition include other antiviral compounds (e.g., cathepsin inhibitors).

Compositions according to the embodiments disclosed herein are useful in treating and/or preventing viral infection from caliciviruses (noroviruses), picornaviruses, and/or coronaviruses in a subject. Thus, embodiments described herein have broad-spectrum therapeutic and/or prophylactic uses. The terms "therapeutic" or "treat," as used herein, refer to processes that are intended to produce a beneficial change in an existing condition (e.g., viral infection, disease, disorder) of a subject, such as by reducing the severity of the clinical symptoms and/or effects of the infection, and/or reducing the duration of the infection/symptoms/effects, and/or reducing viral shedding (e.g., excretion or expulsion of the virus or viral particles from an infected subject) and/or reducing the duration of excretion of the virus or viral particles from an infected subject. The terms "prophylactic" or "prevent," as used herein, refer to processes that are intended to inhibit or ameliorate the effects of a future viral infection or disease to which a subject may be exposed (but is not currently infected with). In some cases the composition may prevent the development of observable morbidity from viral infection (i.e., near 100% prevention). In other cases, the composition may only partially prevent and/or lessen the extent of morbidity due to the viral infection (i.e., reduce the severity of the symptoms and/or effects of the infection, and/or reduce the duration of the infection/symptoms/effects). In either case, the compounds are still considered to "prevent" the target infection or disease.

In use, a therapeutically-effective amount of an antiviral compound is administered to a subject. In some embodiments, a composition comprising a therapeutically-effective amount of an antiviral compound is administered to a subject. Regardless, the compound or pharmaceutically acceptable salt thereof will preferably be administered to the subject in an amount sufficient to provide antiviral compound levels (independent of salt, if any) of from about 0.1 mg to about 1,000 mg of compound per kg of body weight of the subject. Thus, it will be appreciated that in the case of compound salts, for example, the formulation may be administered in amounts greater than the above ranges to provide sufficient levels of the active compound.

In some embodiments, the subject is afflicted with or suffering from a condition (e.g., infection, disease, or disorder) before the compounds are administered, wherein methods described herein are useful for treating the condition and/or ameliorating the effects of the condition. In other embodiments, the subject is free of a given condition before administering the compound, wherein the methods described herein are useful for preventing the occurrence or incidence of the condition and/or preventing the effects of the condition, as described above. The disclosed embodiments are suitable for various routes of administration, depending upon the particular carrier and other ingredients used. For example, the prophylactic and/or therapeutic compounds or compositions can be injected intramuscularly, subcutaneously, intradermally, or intravenously. They can also be administered via mucosa such as intranasally or orally. The compounds or compositions can also be administered through the skin via a transdermal patch.

In some embodiments, the compound or compositions can be provided in unit dosage form in a suitable container. The term "unit dosage form" refers to a physically discrete unit suitable as a unitary dosage for human or animal use. Each unit dosage form may contain a predetermined amount of the inventive compound (and/or other active agents) in the carrier calculated to produce a desired effect. In other embodiments, the compound can be provided separate from the carrier (e.g., in its own vial, ampule, sachet, or other suitable container) for on-site mixing before administration to a subject. A kit comprising the antiviral compound(s) is also disclosed herein. The kit further comprises instructions for administering the compound to a subject. The antiviral compound(s) can be provided as part of a dosage unit, already dispersed in a pharmaceutically-acceptable carrier, or it can be provided separately from the carrier. The kit can further comprise instructions for preparing the antiviral compounds for administration to a subject, including for example, instructions for dispersing the compounds in a suitable carrier.

It will be appreciated that therapeutic and prophylactic methods described herein are applicable to humans as well as any suitable non-human animal, including, without limitation, dogs, cats, and other pets, as well as, rodents, primates, horses, cattle, pigs, and non-domestic (i.e., wild) animals, etc. The methods can be also applied for clinical research and/or study. Additional advantages of the various embodiments of the disclosure will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described and claimed herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention. Except where noted, precursor, intermediate, and final compounds described in the synthesis reactions below are independently numbered in each Example.

Example 1

Background of 3C and 3CL Protease Inhibitors of Norovirus and Other Viruses in the Picornavirus-Like Supercluster Noroviruses are a leading cause of food-borne and water-borne non-bacterial acute gastroenteritis. Norovirus infections constitute an important health problem with an estimated 23 million cases of gastroenteritis occurring annually in the U.S., causing 50,000 hospitalizations and 300 deaths. There are currently no effective vaccines or antiviral therapeutics for the treatment of norovirus infection.

Noroviruses are small non-enveloped viruses of the Caliciviridae family. The genome of Norwalk virus (NV), a prototype of noroviruses, consists of a single-stranded, positive sense RNA molecule of ~7.7 Kilo bases that consists of three open reading frames (ORFs) that encode a 200 kDa polyprotein (ORF1), a major capsid protein VP1 (ORF2), and a small basic protein VP2 (ORF3), respectively. The polyprotein is co- and post-translationally processed by a virus-encoded protease to generate mature non-structural proteins. Processing of the polyprotein is mediated by viral 3CL protease of norovirus and this step is essential for virus replication. Similarly, in the replication of other viruses that belong to the Picornavirus-like Supercluster, processing of the viral polyproteins is primarily mediated by viral 3C protease of picornaviruses or 3CL protease of coronaviruses or caliciviruses. Although there is high genetic diversity among these viruses, 3C protease and 3CL protease are highly conserved, as well as essential for virus replication. Inspection of the crystal structures of 3C protease and 3CL protease of these viruses reveals that the proteases share in common a chymotrypsin-like fold, a Cys-His-Glu/Asp catalytic triad (EV and coxsackievirus CV 3C proteases, and NV 3CL protease) or Cys-His dyad (SARS-CoV 3CL protease), an extended binding site, and a preference for cleaving at Gln-Gly (P1-P1') junctions in protein and synthetic peptidyl substrates. The confluence of structural similarities in the active sites, mechanism of action, and substrate specificity preferences of EV and CV 3C proteases, SARS-CoV 3CL protease, and NV 3CL protease (Table 1) suggests that a drug-like entity can be fashioned that displays inhibitory activity against 3C and 3CL proteases, making them appealing targets for the discovery of broad spectrum antiviral agents.

TABLE 1

Substrate specificity of the 3C and 3CL proteases
of viruses in the picornavirus-like supercluster.

| Viral 3C or 3CL protease | $P_5$ | $P_4$ | $P_3$ | $P_2$ | $P_1$ | $P_1'$ | $P_2'$ |
|---|---|---|---|---|---|---|---|
| EV71 | E | A | V/L/T | L/F | Q | G | P |
| CVA16 | E | A | L | F | Q | G | P |
| SARS-CoV | S | A | V/T/K | L | Q | A/S | G |
| NV | D/E | F/Y | H/Q/E | L | Q | G | P |

Peptidomimetics—Inhibitors of 3C and 3CL Protease Inhibitors of Norovirus and Other Viruses in the Picornavirus-Like Supercluster Norovirus 3CL protease is a chymotrypsin-like cysteine protease having a Cys-His-Glu catalytic triad and an extended binding site. The substrate specificity of norovirus 3CL protease has been determined using peptidyl chromogenic and fluorogenic substrates. Our foray in this area focused initially on the design of transition state inhibitors (FIG. 1) of NV 3CL protease that incorporate in their structure a recognition element (a peptidyl fragment) that is congruent with the known substrate specificity of the enzyme and a warhead (aldehyde, α-ketoamide, or α-ketoheterocycle) that interacts with the active site cysteine (Cys139) to form a reversible adduct (FIG. 2). NV 3CL protease shows a strong preference for a -D/E-F/Y-X-L-Q-G sequence (SEQ ID NO:6, where X is Q, H, or E) corresponding to the subsites $S_5$-$S_4$-$S_3$-$S_2$-$S_1$-$S_1'$-(cleavage is at the $P_1$-$P_1'$ [Q-G] scissile bond). The recognition element is responsible for binding and correct positioning of the inhibitor to the active site so that favorable binding interactions (H bonds, hydrophobic and dipole-dipole interactions) are optimal.

Since the primary specificity residue (P1) of norovirus 3CL protease is Gln, initial design considerations included the use of a glutamine surrogate for optimal synthetic tractability and design flexibility. Thus, a series of peptidyl aldehydes (Ia), α-ketoamides (Ib), α-ketoheterocycles (Ic) depicted in FIG. 1, and their bisulfite adducts were synthesized and screened against norovirus 3CL protease enzyme and in a cell-based replicon system. Our initial SAR studies in the peptidyl aldehyde series probed the nature of the P2 residue, since our structural studies suggested that the Leu side chain of the compounds did not optimally fill the S2 pocket. Thus, we furthermore examined the effect of extending the recognition element (dipeptidyl versus tripeptidyl) on potency and permeability of the compounds. In addition, the S1' subsite (and beyond) was probed by varying the nature of the $R^1$ group in the α-ketoamide series (FIG. 1, Ib). Briefly, the results of those studies have demonstrated that (a) dipeptidyl inhibitors Ia-c inhibit norovirus 3CL protease enzyme, as well as norovirus replication in a cell-based replicon system; (b) a P2 residue with an R=n-butyl or cyclohexylmethyl side chain is preferred; (c) an array of structurally diverse $R^1$ groups are tolerated in the α-ketoamide series (FIG. 1, structure Ib); (d) a high resolution X-ray crystal structure of the NV 3CL protease-ligand complex with Ia has been determined and, (e) the bisulfite salt adduct of aldehyde Ia was found to show efficacy in the gnotobiotic pig model of norovirus infection. This is the first time that transition state inhibitors and a high-resolution crystal structure of a transition state inhibitor-enzyme complex, have been reported for norovirus 3CL protease. It is also the first time that bisulfite salt adducts of transition state inhibitors have been shown to inhibit norovirus 3CL protease enzyme, to exhibit anti-norovirus activity in a cell-based replicon system, and to have efficacy in an animal model of norovirus infection.

Based on the aforementioned findings, we will synthesize peptidomimetics II-IV (FIG. 3, Schemes 1-2) that incorporate in their structures an α-ketoamide, α-ketoheterocycle, α-hydroxyphosphonate, bisulfite salt, sulfonamide, or ketone warhead. The biochemical rationale underlying the design of peptidomimetic II (Scheme 1) is based on the following considerations: as stated earlier, one of the preferred $P_3$ residues in NV 3CL protease is Gln. We reasoned that (a) locking the $-CH_2CH_2CO-$ portion of the Gln side chain into a glutamine ring, thereby reducing its conformational mobility, will enhance affinity because of the more favorable entropy upon binding, (b) the lower peptidyl character of inhibitor II will likely enhance cellular permeability and, (c) the inhibitor will still be able to engage in all the anticipated H-bonding and hydrophobic interactions. The synthesis of inhibitor II is outlined in Scheme 1. All peptidyl aldehydes synthesized here and elsewhere in this application are used as active site probes, as well as precursors in the synthesis of the desired α-ketoamides, α-ketoheterocycles, etc. inhibitors. The nature of the R group in II using Nva, Nle, cyclohexylmethyl and t-butyl is probed, and the "cap" is optimized (in terms of physicochemical properties, ADMET and PK properties) by removing the Z group and generating structurally diverse focused libraries of heterocyclic amides, sulfonamides, etc.

The biochemical rationale underlying the design of peptidomimetic III-IV (Scheme 2) is as follows: the 1,2,3-triazole ring, readily generated via a copper-catalyzed azide-alkyne cycloaddition reaction, has recently emerged as a genuine substitute for an amide bond. The structural and electronic characteristics of 1,2,4-triazoles are similar to those of a peptide bond. Thus, 1,2,3-triazoles offer an appealing structural motif in terms of the design of peptidomimetics. The 1,2,3-triazole ring is used as a bioisostere of Gln in the synthesis of norovirus 3CL protease inhibitors (Scheme 2, general structures III-IV). Inhibitors III-IV can be readily assembled via EDCI-mediated coupling of a series of Z-protected amino acids with the azido amino acid ester (Scheme 2) which can be readily synthesized using literature procedures. To our knowledge, this is the first time that the 1,2,3-triazole ring is proposed as a potential bioisostere for Gln in the design of norovirus 3CL protease inhibitors. Importantly, this approach can be extended to other viral cysteine proteases having the same primary substrate specificity, such as HRV 3CL protease, HAV 3CL protease, SARS-CoA 3CL protease, and others.

Macrocyclic Inhibitors of 3C and 3CL Protease of Noroviruses and Other Viruses in the Supercluster.

The biochemical rationale underlying the design of macrocyclic inhibitors is based on the following considerations: (A) Proteases universally recognize their ligands in the β-strand conformation. (B) Macrocyclization is an effective way to restrict/preorganize a peptidyl transition state mimic in a β-turn conformation suitable for binding to the active site of a protease and/or into a conformation closely resembling that found in an enzyme-inhibitor complex. This generally results in higher affinity and selectivity, enhanced permeability, and improved bioavailability. This has been amply demonstrated with mammalian and viral proteases. (C) Macrocyclization increases proteolytic stability and reduces polarity, thereby improving drug-like character. (D) As mentioned earlier, the $S_3$ subsite of norovirus 3CL protease can accommodate Q, H, or E. The plasticity of the $S_3$ subsite is used to design an array of macrocyclic inhibitors V-VIII (FIG. 4, Schemes 3-6) of norovirus 3CL protease by tethering the $P_1$ and $P_3$ residues with or without a linker. Molecular modeling studies indicate that macrocyclic inhibitors V-VIII assume conformations that are readily superimposable on the bound peptidyl ligand in the NV 3CL protease X-ray crystal structure, providing a strong measure of assurance that key binding interactions will be maintained; and, (e) an important consideration related to the selection of the proposed macrocycles is their synthetic tractability. Click chemistry and ring-closing metathesis reactions have a broad scope and high tolerance of other chemical functionalities.

Macrocycle V can be readily constructed as shown in Scheme 3 using commercially available (L)BocNHCH(CH$_2$CH$_2$COOH)COOCH$_3$ and (L)BocNHCH(CH$_2$CH$_2$COOBn)COOH. It is well known that the size of the macrocyclic ring influences the yield of the cyclization step and, more importantly, inhibitory activity; consequently, 15-membered (n=0) and 17-18-membered (n=2-3) macrocyclic inhibitors Va-c, as outlined in Scheme 3, is constructed.

Macrocycle VI tethers the P$_1$ and P$_3$ residues via an electron-rich 1,2,3-triazole having multiple hydrogen bond acceptor (HBA) sites. Because the S$_3$ pocket of NV 3CL protease can accommodate H, Q, or E, the triazole ring in VI is intended to serve as a mimic of the amide bond of the P$_3$ Gln. The triazole ring can be readily generated from a suitable alkyne-azide precursor (Scheme 4). EDCI-mediated coupling of (L)BocNHCH(CH$_2$CH$_2$COOH)COOCH$_3$ with 2-azidoethylamine is followed by removal of the Boc group and subsequent coupling to commercially available Boc-L-propargylglycine. The resulting product is then cyclized using standard click chemistry conditions. The resulting 17-membered macrocycle will then be elaborated further to yield VIa-c derivatives. The corresponding complementary macrocycle VII will be synthesized using a similar reaction sequence (Scheme 5). 3-Azido-N-(t-butoxycarbonyl)-L-alanine can be readily synthesized by treating L-2,3-diaminopropionic acid with triflic anhydride and NaN$_3$. Finally, macrocycle VIII retains and links the P$_3$ His and P$_1$ Q residues with a 4-carbon linker (Scheme 6). The cyclization step employs a ring-closing methathesis reaction. It is anticipated that the outcome will result in several lead compounds (α-ketoamides and α-ketoheterocycles) suitable for further development.

Example 2

Synthesis of Macrocyclic Inhibitors

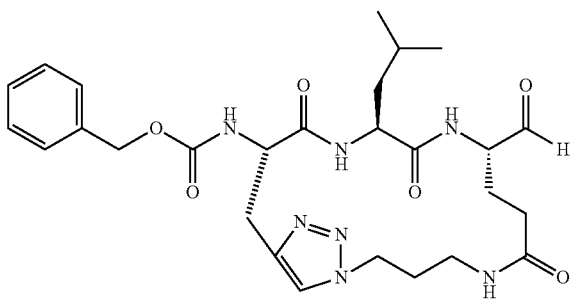 [SMILES: CC(C)C[C@@H]1NC(=O)[C@@H](NC(=O)OCc2ccccc2)Cc2cn(nn2)CCCNC(=O)CC[C@@H](C=O)NC1=O]

Figure 5:
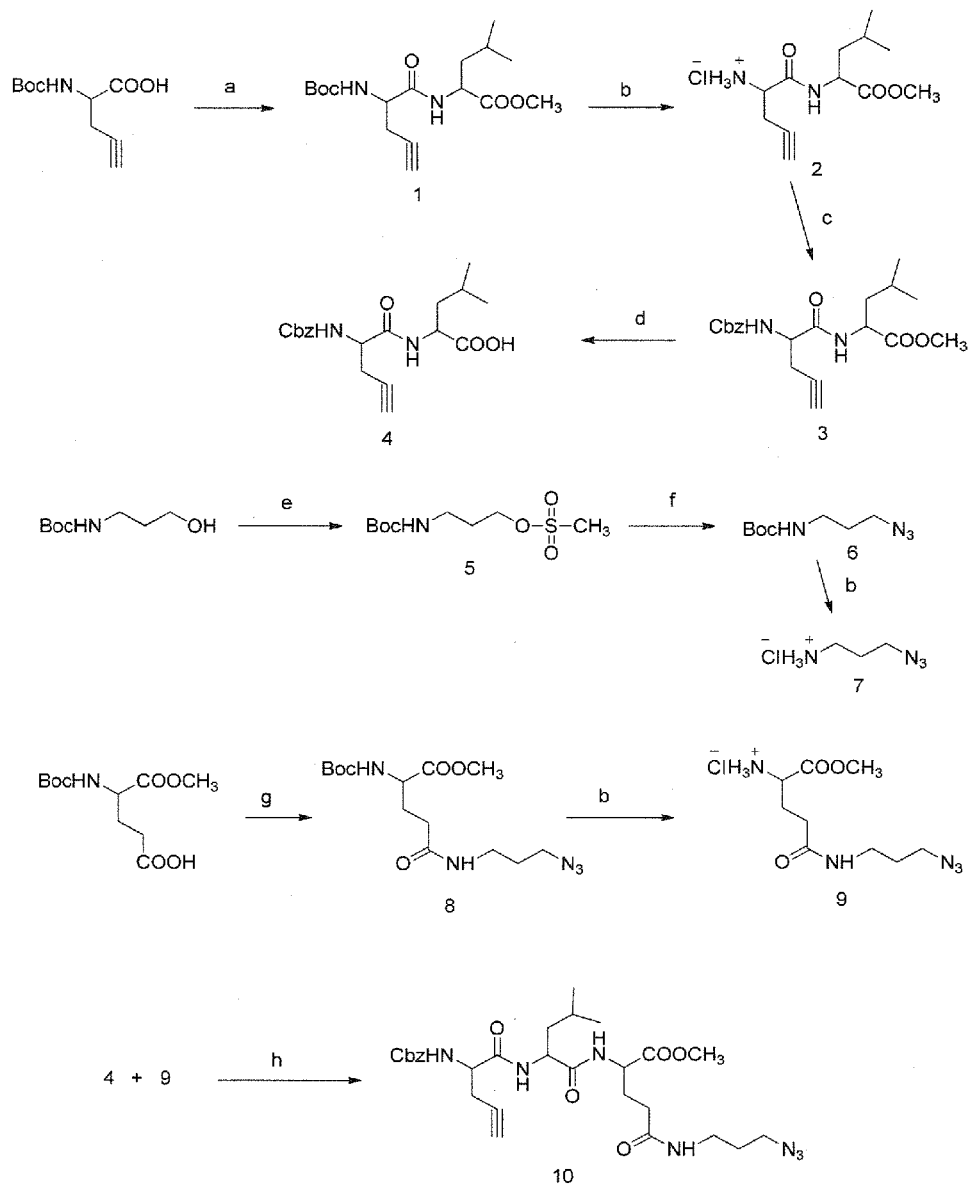
FIG. 5 shows the reaction scheme for synthesizing the macrocyclic inhibitor described in Example 2.
Figure 5:
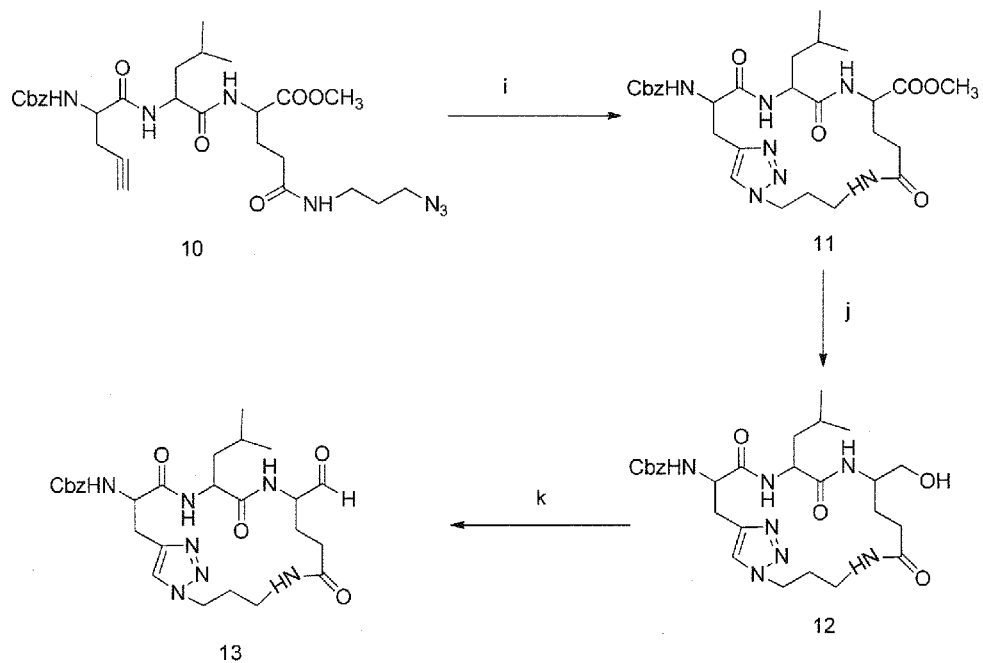

Based on the aforementioned considerations, a macrocyclic inhibitor was assembled in a convergent fashion by first constructing fragments 4 and 9, followed by subsequent coupling of the two fragments to generate acyclic precursor 10 (FIG. 5). Cyclization was subsequently accomplished using click chemistry.

Materials and Methods

The $^1$H NMR spectra were recorded on a Varian XL-300 or XL-400 NMR spectrometer. Melting points were determined on a Mel-Temp apparatus and are uncorrected. Reagents and solvents were purchased from various chemical suppliers (Aldrich, Acros Organics, TCI America, and Bachem). Silica gel (230-450 mech) used for flash chromatography was purchased from Sorbent Technologies (Atlanta, Ga.). Thin layer chromatography was performed using Analtech silica gel. The TLC plates for all the compounds were eluted using two different solvent systems and visualized using iodine and or UV light. Each individual compound was identified as a single spot on TLC plate (purity was >95% as evidenced by $^1$H NMR and/or HPLC analysis).

Synthesis

Methyl 2-(2-((tert-butoxycarbonyl)amino)pent-4-ynamido)-4-methylpentanoate 1

To a solution of Boc-L-propargylglycine (26.65 g; 125 mmol) in dry DMF (170 mL) was added EDCI (29.23 g; 152.5 mmol) and HOBt (23.5 g; 122.5 mmol), and the reaction mixture was stirred at room temperature for 40 min (solution A). In a separate RB flask, (L) Leu-OMe hydrochloride (22.72 g; 125 mmol) in dry DMF (82 mL) kept at 0° C. was treated with diisopropyl ethyl amine (DIEA) (64.62 g; 500 mmol) and the solution was stirred for 25 min (solution B). Solution B was added to solution A and the reaction mixture was stirred overnight at room temperature. The solvent was removed on the rotary evaporator and the residue was taken up in dichloromethane (DCM) (600 mL) and washed sequentially with saturated sodium bicarbonate (2×200 mL), 5% HCl (2×200 mL) and brine (200 mL). The organic layer was dried over anhydrous sodium sulfate, filtered and concentrated, leaving a crude product which was purified using flash chromatography (silica gel; hexane/ethyl acetate 75:25) to give 1 as a white solid (38.12 g; 89% yield); $^1$H NMR (CDCl$_3$) δ 8.2 (s, 1H), 7.0 (s, 1H), 4.3 (m, 1H), 4.1 (m, 1H), 3.6 (s, 3H), 2.8 (s, 1H), 2.4 (m, 2H), 2.3 (m, 1H), 1.6 (m, 2H), 1.5 (m, 1H), 1.38 (s, 9H), 0.87 (d, 6H).

1-((1-Methoxy-4-methyl-1-oxopentan-2-yl)amino)-1-oxopent-4-yn-2-aminium chloride 2

A solution of compound 1 (10.55 g; 31 mmol) in DCM (100 mL) was treated with 4M HCl in dioxane (78 mL; 0.31 mol) and stirred at room temperature for 3 h while monitoring the disappearance of the starting material by TLC. The solvent was removed on the rotary evaporator and the residue was treated with ether and then concentrated to give 2 as an off white solid (8.3 g; 96% yield).

Methyl 2-(2-(((benzyloxy)carbonyl)amino)pent-4-ynamido)-4-methylpentanoate 3

To a solution of compound 2 (8.5 g; 31 mmol) in dry THF (100 mL) was added DIEA (16.02 g; 124 mmol) and the reaction mixture was stirred for 30 min at room temperature. Benzylchloroformate (6.87 g; 40.3 mmol) was added and stirring was continued at room temperature for 16 h. The solvent was removed on the rotary evaporator and the residue was taken up in ethyl acetate (150 mL) and washed sequentially with water (50 mL), 5% HCl (2×50 mL), and brine (50 mL). The organic layer was dried over anhydrous sodium sulfate, filtered and concentrated to give 3 as a white solid (10.46 g; 90% yield). $^1$H NMR (CDCl$_3$) δ 7.3 (m, 5H), 6.7 (s, 1H), 5.6 (s, 1H), 5.1 (s, 2H), 4.6 (m, 1H), 4.4 (m, 1H), 3.7 (s, 3H), 2.6 (m, 2H), 2.8 (s, 1H), 2.6 (m, 1H), 1.6 (m, 2H), 1.5 (m, 1H), 0.9 (d, 6H).

2-(2-(((Benzyloxy)carbonyl)amino)pent-4-ynamido)-4-methylpentanoic acid 4

A solution of compound 3 (10.85 g; 29 mmol) in dry THF (100 mL) kept in an ice bath was treated with a solution of 1M lithium hydroxide (100 mL) and stirred for 4 h at 0° C. until the starting material disappeared (as shown by TLC). The solvent was removed and the residue was diluted with water (25 mL). The pH of the aqueous solution was adjusted to ~2 with 5% HCl and the solution was extracted with ethyl acetate (2×250 mL) and washed with brine (100 mL). The organic extract was dried over anhydrous sodium sulfate, filtered and concentrated, yielding a crude product which was purified by flash chromatography (silica gel; hexane/ethyl acetate 50:50) to give 4 as a white solid (8.8 g; 84% yield). $^1$H NMR (DMSO-d6) δ 8.1 (s, 1H), 7.5 (s, 1H), 7.3 (m, 5H), 5.0 (s, 2H), 4.4 (m, 1H), 4.2 (m, 1H), 2.8 (s, 1H), 2.5 (m, 1H), 2.4 (m, 1H), 1.6 (m, 2H), 1.4 (m, 1H), 0.8 (d, 6H)

3-((Tert-butoxycarbonyl)amino)propyl methanesulfonate 5

To a solution of 3-(Bocamino)-1-propanol (10.51 g: 60 mmol) and TEA (6.07 g; 60 mmol) in dry DCM (100 mL) kept in an ice bath (0° C.) was slowly added methane sulfonyl chloride (6.87 g; 60 mmol) and the reaction mixture was stirred for 30 min at 0° C. The ice bath was removed and the reaction mixture was allowed to stir at room temperature for 5 h (completion of the reaction was monitored by TLC). Water (50 mL) was added with stirring and the resulting mixture was transferred to a reparatory funnel, the layers were separated, and the aqueous layer was extracted with DCM (2×75 mL). The combined organic layers were washed with brine (50 mL), dried over anhydrous sodium sulfate, and concentrated to yield compound 5 as a colorless oil (12.82 g: 100% yield). $^1$H NMR (CDCl$_3$) δ 4.8 (s, 1H), 4.3 (m, 1H), 3.3 (m, 2H), 3.2 (m, 2H), 1.9 (m, 2H), 1.4 (s, 9H).

tert-Butyl(3-azidopropyl)carbamate 6

To a solution of compound 5 (12.56 g: 60 mmol) in dry DMF (150 mL) was added in small portions NaN$_3$ (11.7 g: 180 mmol) with stirring over 30 min. The resulting solution was heated to 50° C. for 1 h and then stirred overnight at room temperature. Water (50 mL) was added with stirring, the solvent was removed, and the residue was extracted with ethyl acetate (2×175 mL). The combined organic layers were washed sequentially with water (2×50 mL) and brine (2×50 mL). The organic extract was dried over anhydrous sodium sulfate and evaporated to give compound 6 as a light yellow oil (10.54 g; 87% yield). $^1$H NMR (CDCl$_3$-d6) δ 4.9 (s, 1H), 3.3 (m, 2H), 3.2 (m, 2H), 1.7 (m, 2H), 1.4 (s, 9H).

3-Azidopropan-1-aminium chloride 7

A solution of compound 6 (10.01 g: 50 mmol) in dry DCM (20 mL) was treated with 4M HCl in dioxane (125 mL; 500 mmol) and stirred at room temperature for 3 h while monitoring the disappearance of the starting material by TLC. The solvent was removed on the rotary evaporator and the residue was treated with ether and concentrated to give compound 7 as a yellow oil (6.7 g; 99% yield).

Methyl 5-((3-azidopropyl)amino)-2-((tert-butoxycarbonyl)amino)-5-oxopentanoate 8

To a solution of (L) BocNH-Glu-OMe (9.67 g; 37 mmol) in dry DMF (100 mL) was added EDCI (8.65 g; 41.1 mmol), HOBt (6.91 g; 45.14 mmol), and the reaction mixture was stirred at room temperature for 1 h (solution A). In the meantime, to a solution of compound 7 (5.05 g: 37 mmol) in dry DMF (50 mL) kept at 0° C. was added DIEA (23.9 g; 185 mmol) and stirred for 30 min (solution B). Solution B was added to solution A and the reaction mixture was stirred overnight at room temperature. The solvent was removed on the rotary evaporator and the residue was taken up in DCM (400 mL) and washed sequentially with 10% citric acid (100 mL) and brine (100 mL). The organic layer was dried over anhydrous sodium sulfate, filtered, and concentrated, yielding a crude product was purified by flash chromatography (silica gel; hexane/ethyl acetate 70:30) to give 1 as a white solid (8.6 g; 67% yield). $^1$H NMR (CDCl$_3$) δ 7.8 (s, 1H), 7.4 (s, 1H), 4.6 (m, 1H), 3.7 (s, 3H), 3.3 (t, 1H), 2.2 (m, 2H), 2.1 (m, 2H), 1.9 (m, 2H), 1.7 (m, 2H), 1.4 (s, 9H).

5-((3-Azidopropyl)amino)-1-methoxy-1,5-dioxopentan-2-aminium chloride 9

A solution of compound 8 (4.4 g: 15 mmol) in dry DCM (20 mL) was treated with 4M HCl in dioxane (37 mL; 150 mmol) and stirred at room temperature for 3 h while monitoring the disappearance of the starting material by TLC. The solvent was removed on the rotary evaporator and the residue was treated with ether and concentrated to give compound 7 as a yellow oil (4.0 g; 95% yield).

Methyl 11-(3((3-azidopropyl)amino)-3-oxopropyl)-8-isobutyl-3,6,9-trioxo-1-phenyl-5-(prop-2-yn-1-yl)-2-oxa-4,7,10-triazadodecan-12-oate 10

To a solution of compound 4 (11.7 g; 31 mmol) in dry DMF (100 mL) was added EDCI (7.25 g; 37.82 mmol), HOBt (5.79 g; 37.82 mmol), and the reaction mixture was stirred at room temperature for 30 min (solution A). In the meantime, to a solution of compound 9 (8.67 g: 31 mmol) in dry DMF (100 mL) kept at 0° C. was added DIEA (10.01 g; 77.7 mmol) and stirred for 30 min (solution B). Solution B was mixed with solution A and the reaction mixture was stirred overnight at room temperature. The solvent was removed on the rotary evaporator and the residue was taken up in ethyl acetate (300 mL) and washed sequentially with saturated sodium bicarbonate (2×75 mL), 5% HCl (2×75 mL) and brine (75 mL). The organic layer was dried over anhydrous sodium sulfate, filtered, and concentrated, yielding a crude product which was purified using recrystallization to yield 9 as an off white solid (8.3 g; 46% yield). NMR (CDCl$_3$) δ 8.1 (s, 1H), 7.9 (s, 1H), 7.8 (s, 1H), 7.5 (s, 1H) 7.3 (m, 5H), 5.0 (s, 2H), 4.3 (m, 1H), 4.1 (m, 1H), 3.3 (t, 1H), 2.8 (s, 1H), 2.4 (d, 2H), 2.2 (d, 2H), 2.1 (m, 2H), 1.9 (m, 2H), 1.8 (m, 2H), 1.6 (m, 2H), 1.4 (m, 1H), 0.8 (d, 6H)

Methyl 15-(((benzyloxy)carbonyl)amino)-12-isobutyl-6,11,14-trioxo-1,5,10,13,18,19-hexaazabicyclo[15.2.1]icosa-17(20),18-diene-9-carboxylate 11

To a solution of compound 10 (0.3 g: 0.512 mmol) in dry DCM (420 mL) under N$_2$ atmosphere, was added DBU (0.233 g; 1.53 mmol) at room temperature with vigorous stirring. After 15 min, Cu(I)Br (0.073 g; 0.512 mmol) was added and the reaction mixture was stirred for 12 h at room temperature. The reaction mixture was quenched by adding 3M HCl (100 mL) and the aqueous layer was separated and extracted with DCM (2×500 mL). The combined organic layers were washed with brine (300 mL), and dried over anhydrous sodium sulfate. The solution was filtered and concentrated to give a crude product which was purified using flash chromatography (silica gel; methylene chloride/methanol 99:1) to give compound 11 as a white solid (0.14 g; 45% yield). $^1$H NMR (DMSO-d6) δ 8.5 (s, 1H), 8.1 (s, 1H), 7.5 (s, 1H), 7.3 (m, 5H), 5.0 (m, 2H), 4.3 (m, 1H), 4.1 (m, 2H), 3.6 (m, 2H), 3.3 (s, 3H), 3.11 (m, 2H), 2.88 (m, 2H), 2.98-2.24 (m, 5H), 1.49-1.8 (m, 5H), 0.86 (m, 6H).

Benzyl 9-(hydroxymethyl)-12-isobutyl-6,11,14-trioxo-1,5,10,13,18,19-hexaazabicyclo[15.2.1]icosa-17(20),18-dien-15-yl)carbamate 12

To a solution of compound 11 (0.58 g: 1 mmol) in dry THF (6 mL) was added a solution of 2M LiBH$_4$ (1.5 mL; 3.0 mmol) dropwise followed by the dropwise addition of absolute ethanol (11 mL) at room temperature with stirring. After the reaction mixture was stirred for 16 h (the disappearance of the starting material was monitored by TLC), the solvent was removed on the rotary evaporator and the residue was partitioned between ethyl acetate and 1M KHSO$_4$. The aqueous phase was extracted twice with chloroform (2×25 mL) and each organic extract was washed with brine separately, dried over anhydrous sodium sulfate, and evaporated to give compound 12 as a white solid (0.47; 84% yield). $^1$H NMR (DMSO-d6) δ 8.1 (s, 1H), 7.91 (s, 1H), 7.62 (s, 1H), 7.31 (m, 5H), 5.13 (m, 2H), 4.50 (m, 1H), 4.4-4.8 (s, 1H) 4.4 (m, 2H), 3.8 (m, 2H), 3.11 (m, 2H), 2.88 (m, 2H), 2.98-2.24 (m, 5H), 1.37-1.7 (m, 5H), 0.81 (m, 6H).

Benzyl(9-formyl-12-isobutyl-6,11,14-trioxo-1,5,10,13,18,19-hexaazabicyclo[15.2.1]icosa-17(20),18-dien-15-yl)carbamate 13

Compound 13 (66.84 mg: 0.12 mmol) was suspended in dry DCM (40 mL) under a N$_2$ atmosphere and Dess-Martin periodinane reagent (1.08 g; 0.36 mmol) was added. The reaction mixture was stirred for 4 h at room temperature and quenched with saturated sodium bicarbonate solution containing 10% sodium thiosulfate (10 mL). The organic layer was separated and the aqueous layer was extracted with DCM (2×60 mL). The combined organic layers were washed with brine (40 mL), dried over anhydrous sodium sulfate, and concentrated. The crude product was purified using flash chromatography (silica gel; methylene chloride/methanol 99:1) to give macrocyclic aldehyde 13 as an off white solid (47 mg; 71% yield). $^1$H NMR (DMSO-d6) δ 9.49 (s, 1H), 7.83 (s, 1H), 7.3 (m, 5H), 5.1 (m, 2H), 4.5 (m, 1H), 4.4 (m, 2H), 3.8 (m, 2H), 3.11 (m, 2H), 2.88 (m, 2H), 2.98-2.24 (m, 5H), 1.49-1.8 (m, 5H), 0.81-0.99 (m, 6H). HRMS: calcd for C$_{27}$H$_{37}$N$_7$O$_6$Na ([M+Na]$^+$) 578.2703. found 578.2702 ([M+Na]$^+$).

Example 3

Evaluation of Inhibitors of 3C and 3CL Proteases of Viruses in the Supercluster

Figure 6:
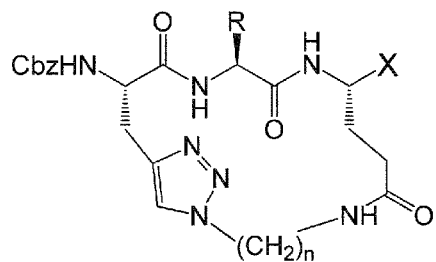
FIG. 6 shows a general structure for derivatives of the macrocylic inhibitor described in Example 2 and used as a norovirus inhibitor in Example 3.

The inhibitory activity of aldehyde 13 (FIG. 6) was evaluated in vitro. The codon-optimized cDNAs for 3C protease or 3CL protease of NV, SARS-CoV, and EV71 were synthesized fused with 6 His at the N-terminal (Genscript, Piscataway, N.J.). Each synthesized gene or amplified product was then subcloned into the pET-28a(+) vector. 3C protease and 3CL protease were then expressed and purified using standard methods before being evaluated using fluorescence resonance energy transfer (FRET) protease assays.

The designation of substrate residues for P1 and P1' started at the scissile bond and counting towards the N- or C-termini, respectively. The FRET protease assay was performed as follows. Stock solutions (10 mM) of the substrates and the compounds were prepared in dimethyl sulfoxide (DMSO) and diluted in assay buffer. The assay buffer comprised 20 mM HEPES buffer containing NaCl, EDTA, Glycerol, and dithiothreitol (DTT) at pH 6 (SARS-CoV 3CL protease) or 8 (NV and EV71). Each protease was mixed with serial dilutions of each compound or with DMSO in 25 µl of assay buffer and incubated at 37° C. for 30 min, followed by the addition of 25 µl of assay buffer containing substrate. Fluorogenic substrates with Edans and Dabcyl as a donor and quencher pair were purchased from Bachem (SARS-CoV substrate) or synthesized by GenScript. The viral proteases and the corresponding fluorogenic substrates are listed in Table 2.

TABLE 2

Virus proteases and fluorogenic substrates used for FRET protease assays

| | | | Buffer conditions | | |
|---|---|---|---|---|---|
| Virus family and virus[4] | Fluorogenic substrates | pH | Glycerol (%) | DTT (mM) | NaCl (mM) |
| *Caliciviridae*/ NV | Edans-DFHLQ/GP-Dabcyl (SEQ ID NO: 1) | 8 | 60 | 6 | 120 |
| *Coronaviridae*/ SARS-CoV | Dabcyl-KTSAVLQ/ SGFRKME-Edans (SEQ ID NO: 2) | 6 | 30 | 4 | 120 |
| *Picornaviridae*/ EV71 | Dabcyl-KTSAVLQ/ SGFRKME-Edans (SEQ ID NO: 2) | 8 | 20 | 4 | 120 |

[4]NV: norovirus strain Norwalk; SARS-CoV: severe acute respiratory syndrome coronavirus; EV71; enterovirus 71.

Fluorescence readings were obtained using an excitation wavelength of 360 nm and an emission wavelength of 460 nm on a fluorescence microplate reader (FLx800; Biotek, Winooski, Vt.) at 1 h following the addition of substrate. The relative fluorescence units (RFU) were determined by subtracting background values (substrate-containing well without protease) from the raw fluorescence values as described previously. The dose-dependent FRET inhibition curves were fitted with a variable slope by using GraphPad Prism software (GraphPad, La Jolla, Calif.) in order to determine the $IC_{50}$s of compounds. Aldehyde 13 displayed inhibitory activity against NV 3CL protease ($IC_{50}$ 5.1 µM), EV71 3C protease ($IC_{50}$ 1.8 µM), and SRAS-CoV 3CL protease ($IC_{50}$ 15.5 µM).

Figure 7:
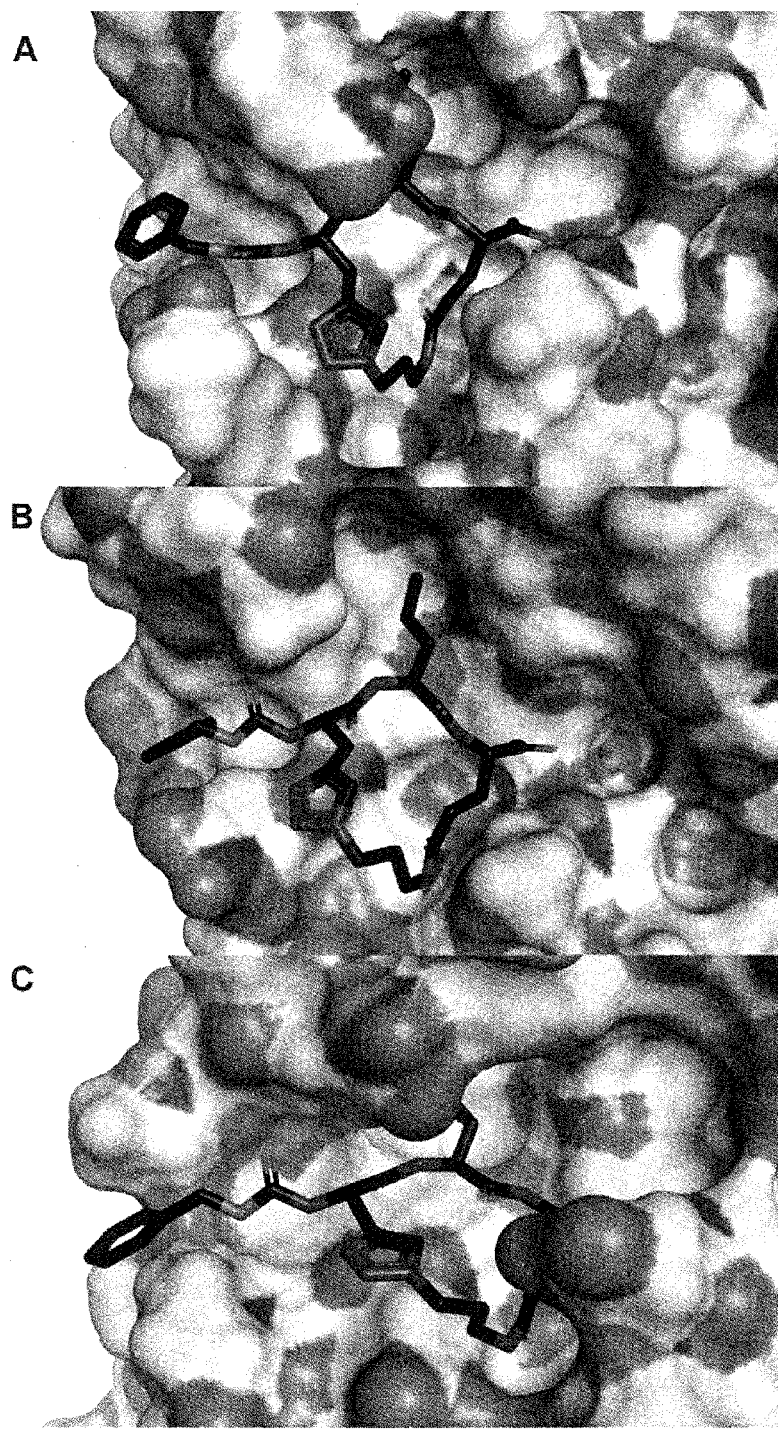
FIG. 7 illustrates computationally predicted binding modes for inhibitor 13 bound to A) Norovirus 3CL protease, B) Coxsackie virus 3C protease, and C) SARS-CoV 3CL protease, from Example 3. Inhibitor 13 is rendered as CPK-colored sticks with black carbon atoms. Protein receptors are shown as Connolly surfaces colored as follows: yellow=nonpolar aryl, alkyl and thioalkyl; white=weakly polar aryl and alkyl; cyan=polar H; blue=polar N; and red=polar O.

In order to gain insight and understanding into the binding of inhibitor 8 to the active site of each protease, computer modeling was used (FIG. 7). Thus, the receptor structures were prepared from the following protein data bank (PDB) crystal structures: A) NV 3CL protease from 2IPH; B) CV 3C protease from 3ZZB; and C) SARS-CoV 3CL protease from 2ZU5. These three receptor models were chosen by virtue of having co-crystallized ligands that each displayed the following three features consistent with the likely binding mode of inhibitor 13: i) a covalent attachment to the catalytically active cysteine (analogous to the terminal aldehyde in inhibitor 13); ii) branched alkyl, as per isobutyl group in 13; and iii) aryl (phenylalanine or Cbz), as per Cbz in 13. This permitted the intelligent prepositioning of inhibitor 13 into each of the three protease receptors, which was accomplished in Pymol via manual docking. Pymol was then used to produce a computational framework for refining the docked conformation as follows: a ligand-receptor complex was generated by protonating the preliminary receptor-ligand complex (according to physiological pH with anionic aspartate and glutamate residues, and cationic lysine and arginine residues), then retaining only the ligand plus all complete residues with at least one atom located within no more than 6.0 Å from any ligand atom. The resulting complex models were then permitted to undergo 1000 molecular mechanics optimization steps in Avogadro using the MMFF94 force field and electrostatic charge model. The resulting complexes were then rendered in PyMol. The computational studies indicate that inhibitor 13 is capable of nestling snugly in the active site of the 3C and 3CL proteases.

In summary, we report herein for the first time the inhibition of the 3C protease and 3CL protease of viral pathogens belonging to the picornavirus-like supercluster by a macrocyclic inhibitor.

Example 4

Synthesis of Peptidomimetic Inhibitors

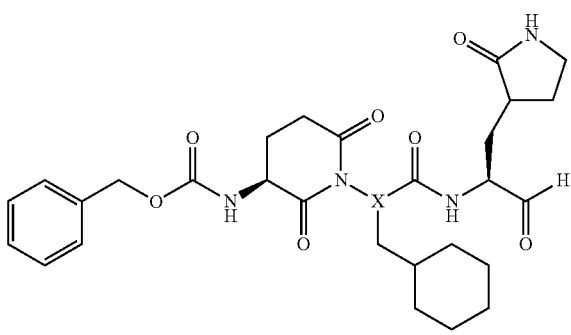

Figure 8:
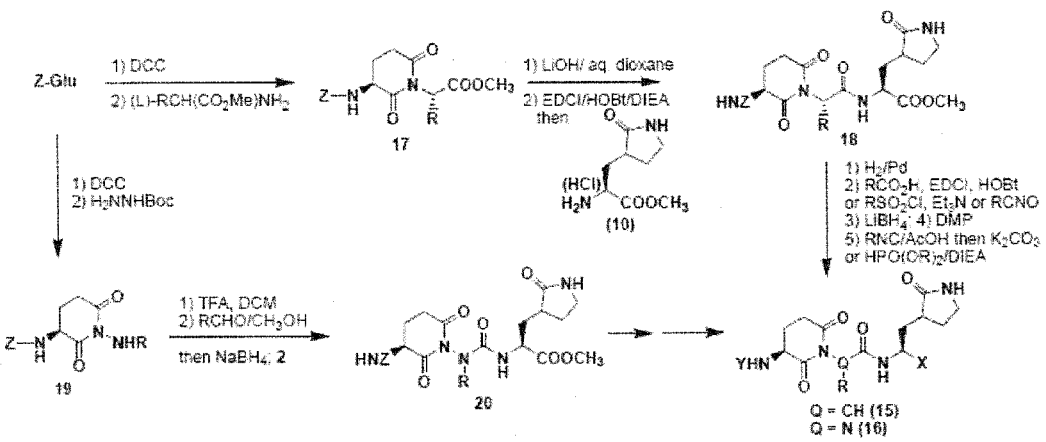
FIG. 8 shows the reaction scheme for synthesizing a peptidomimetic derivative.
Figure 9:
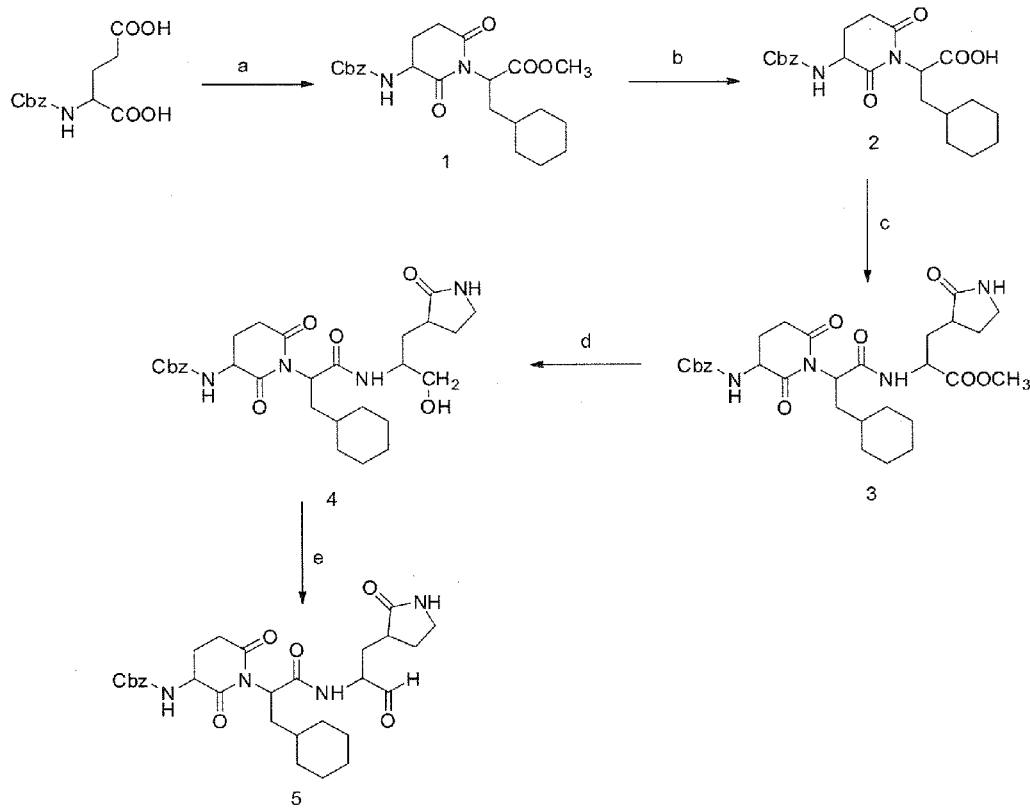
FIG. 9 shows the reaction scheme used to synthesize a peptidomimetic inhibitor in Example 4.

In this Example, the synthesis of peptidomimetic inhibitors is proposed (FIG. 8, where Q is CH (compound 15) or N (compound 16), and R is cyclohexylmethyl), and the synthesis of a peptidomimetic compound is described (FIG. 9). The biochemical rationale underlying the design of peptidomimetics is based on the following considerations: (a) the S3 subsite of 3CL protease exhibits considerable plasticity (Table 1, supra) and one of the preferred P3 residues is Gln; (b) locking the —$CH_2CH_2CO$— portion of the Gln side chain into a ring, thereby reducing its conformational mobility, will enhance affinity because of the more favorable entropy upon binding; (c) in the proposed reaction scheme the lower peptidyl character of compound 15 (see FIG. 8, where Q=CH) will also likely enhance cellular permeability; (d) compounds 15 (Q=CH) and 16 (Q=N) are capable of engaging in all the anticipated H-bonding and hydrophobic interactions (data not shown); and (e) peptidomimetic 16 is a stereochemically-robust azapeptide variant of 15.

We recently demonstrated (see Example 5 below) that compound 15 (Y=Cbz, R=cyclohexylmethyl, and X=CHO) potently inhibits NV in replicon-harboring cells ($EC_{50}$ 0.9 µM) and other viruses in the supercluster at low micromolar concentrations in cell culture. The actual synthesis of a variant of compound 15 is illustrated in FIG. 9 (compound 5) and described in detail below.

Materials and Methods

The $^1$H NMR spectra were recorded on a Varian XL-300 or XL-400 NMR spectrometer. Melting points were determined on a Mel-Temp apparatus and are uncorrected. Reagents and solvents were purchased from various chemical suppliers (Aldrich, Acros Organics, TCI America, and Bachem). Silica gel (230-450 mech) used for flash chromatography was purchased from Sorbent Technologies (Atlanta, Ga.). Thin layer chromatography was performed using Analtech silica gel. The TLC plates for all the compounds were eluted using two different solvent systems and visualized using iodine and/or UV light. Each individual compound was identified as a single spot on TLC plate and the purity was >95% as evidenced by $^1$H NMR and/or HPLC analysis.

Synthesis

Methyl 2-(3-(((benzyloxy)carbonyl)amino)-2,6-dioxopiperidin-1-yl)-3-cyclohexyl-propanoate 1

To a solution of (L) N-Cbz-glutamic acid (5.62 g; 20 mmol) in dry DMF (100 mL) was added HATU (8.36 g; 22 mmol) and DMAP (0.56 g) followed by the dropwise addition of TEA (6 mL; 44 mmol). The reaction mixture was stirred at room temperature for 1 h (solution A). In the meantime, to a solution of (L) cyclohexylalanine-OMe(HCl) (5.32 g; 24 mmol) in dry DMF (30 mL) was added DIEA (9.28 g; 72 mmol) and the reaction mixture was stirred for 15 min (solution B). Solution B was mixed with solution A and stirred overnight at room temperature. The solvent was removed on the rotary evaporator and the residue was taken up in ethyl acetate (300 mL). The organic layer was washed sequentially with saturated sodium bicarbonate (2×100 mL), 5% HCl (2×100 mL) and brine (100 mL). The organic layer was dried over anhydrous sodium sulfate, filtered and concentrated, yielding a crude product which was purified by flash chromatography (silica gel; hexane/ethyl acetate 75:25) to give 1 as a white solid (2.15 g; 32% yield). $^1$H NMR (CDCl$_3$): δ 8.0 (s, 1H), 7.32 (m, 5H), 5.04 (m, 2H), 4.62 (m, 1H), 4.0 (m 1H), 3.73 (s, 3H), 2.3 (m, 2H), 2.0 (m, 2H), 1.65 (m, 6H), 1.46 (m, 1H), 1.18 (m, 4H), 0.89 (m, 2H).

2-(3-(((Benzyloxy)carbonyl)amino)-2,6-dioxopiperidin-1-yl)-3-cyclohexylpropanoic acid A solution of compound 1 (2.75 g: 6.4 mmol) in dry THF (25 mL) was treated with a solution of 1M lithium hydroxide (22 mL) and stirred for 4 h at room temperature until the starting material disappeared (as shown by TLC). The solvent was removed in vacuo and the residue was diluted with water (25 mL). The pH of the aqueous solution was adjusted to ~2 with 5% HCl and the solution was extracted with ethyl acetate (2×100 mL) and washed with brine (30 mL). The organic extract was dried using anhydrous sodium sulfate, filtered and concentrated, yielding a crude product which was purified by flash chromatography (silica gel; hexane/ethyl acetate 50:50) to give 2 as a white solid (2.25 g; 84% yield). $^1$H NMR (CDCl3): δ 12.01 (s, 1H), 8.0 (s, 1H), 7.32 (m, 5H), 5.04 (m, 2H), 4.62 (m, 1H), 4.0 (m 1H), 2.3 (m, 2H), 2.0 (m, 2H), 1.65 (m, 6H), 1.46 (m, 1H), 1.18 (m, 4H), 0.89 (m, 2H).

Methyl 2-(2-(3-(((benzyloxy)carbonyl)amino)-2,6-dioxopiperidin-1-yl)-3-cyclohexyl-propanamido)-3-(2-oxopyrrolidin-3-yl)propanoate 3

To a solution of compound 2 (2.09 g; 5 mmol) in dry DMF (20 mL) was added EDCI (1.17 g; 6.1 mmol) and HOBt (0.93 g; 6.1 mmol), and the reaction mixture was stirred at room temperature for 1 h (solution A). In a separate RB flask, to a solution of N-deprotected glutamine surrogate (1.20 g; 5 mmol) in dry DMF (10 mL) kept at 0° C. was added DIEA (2.6 g; 20 mmol) and stirred for 30 min (solution B). Solution B was transferred to solution A and the reaction mixture was stirred overnight at room temperature. The solvent was removed on the rotary evaporator and the residue was taken up in ethylacetate (200 mL) and washed sequentially with saturated sodium bicarbonate (2×50 mL) 5% HCl (2×50 mL) and brine (50 mL). The organic layer was dried over anhydrous sodium sulfate, filtered, and concentrated, yielding a crude product which was purified by flash chromatography (silica gel; hexane/ethyl acetate 50:50) to give 3 as a white solid (1.98 g; 68% yield). $^1$H NMR (CDCl3): δ 7.32 (m, 5H), 5.04 (m, 2H), 4.45 (m, 2H), 3.73 (s, 3H), 3.26 (m, 2H), 2.3 (m, 4H), 2.0 (m, 2H), 1.65 (m, 8H), 1.46 (m, 1H), 1.18 (m, 4H), 0.89 (m, 2H).

Benzyl(1-(3-cyclohexyl-1-((1-hydroxy-3-(2-oxopyrrolidin-3-yl)propan-2-yl)amino)-1-oxopropan-2-yl)-2,6-dioxopperidin-3-yl)carbamate 4

To a solution of compound 3 (0.22 g: 0.37 mmol) in dry THF (3 mL) was added dropwise a solution of 2M LiBH$_4$ (0.55 mL; 1.11 mmol), followed by the dropwise addition of absolute ethanol (2 mL). The reaction mixture was stirred at room temperature for 16 h while monitoring the disappearance of the starting material by TLC. The solvent was removed on the rotary evaporator and the residue was partitioned between ethyl acetate (75 mL) and 1M KHSO$_4$ (25 mL). The aqueous phase was extracted twice more with chloroform and each organic extract was washed with brine separately, dried over anhydrous sodium sulfate and evaporated to give compound 4 as a white solid (0.18; 87% yield). $^1$H NMR (DMSO-d$_6$) δ 7.32 (m, 5H), 5.04 (s, 2H), 4.3 (m, 2H), 4.18 (m, 1H), 4.0 (m 1H), 3.76 (m, 1H), 2.8 (m, 1H), 2.0 (m, 2H), 1.65 (m, 6H), 1.46 (m, 1H), 1.18 (m, 4H), 0.89 (m, 2H).

Benzyl(1-(3-cyclohexyl-1-oxo-1-((1-oxo-3-(2-oxopyrrolidin-3-yl)propan-2-yl)amino) propan-2-yl)-2,6-dioxopperidin-3-yl)carbamate 5

To a mixture of compound 4 (66.79 mg: 0.12 mmol) in dry DCM (40 mL) kept under a N$_2$ atmosphere was added Dess-Martin periodinane (1.08 g; 0.36 mmol) at room temperature with stirring. The reaction mixture was stirred for 4 h and quenched with a saturated sodium bicarbonate solution containing 10% sodium thiosulfate (10 mL). The organic layer was separated and the aqueous layer was extracted with DCM (2×60 mL). The combined organic layers were washed with brine (40 mL), dried over anhydrous sodium sulfate and concentrated, leaving a crude product which was purified using flash chromatography (silica gel; methylene chloride/methanol 95:5) to give peptidomimetic 5 as an white solid (32 mg; 48% yield). $^1$H NMR (DMSO-d$_6$) δ 9.4 (s, 1H), 8.0 (s, 1H), 7.32 (m, 5H), 5.04 (s, 2H), 4.3 (m, 2H), 4.18 (m, 1H), 4.0 (m 1H), 3.76 (m, 1H), 2.8 (m, 1H), 2.0 (m, 2H), 1.65 (m, 6H), 1.46 (m, 1H), 1.18 (m, 4H), 0.89 (m, 2H).

Example 5

Evaluation of the Compounds in Cell-Based Assays

In the present example, the ability of the compounds to inhibit NV and other viruses in the supercluster in cell culture system was tested. Compound 5 did not show any toxicity to cells up to 150 μM.

TABLE 3

Viruses used for cell-based screening assay.

| Virus family | Viruses | Cell lines |
| --- | --- | --- |
| Calicivirus | Norwalk virus | HG23 |
|  | FCV | CRFK |
|  | MNV-1 | RAW267.4 |
| Coronaviridae | TGEV | ST |
|  | FIPV | CRFK |
|  | 229E | MRC-5 |
|  | MHV | CCL-9.1 |
|  | BCV | HRT18 |
| Picornaviridae | Teschovirus | ST |
|  | Enterovirus 71 | Vero |

The effects of each compound on the viral replication were examined. The list of viruses and corresponding cell lines are listed above in Table 3. Briefly, confluent cells were inoculated with virus at a MOI of 5 or 0.05 for 1 hr, and medium was replaced with medium containing mock-medium or each compound (up to 100 μM). The virus infected cells were further incubated for up to 96 hrs, and the replication of virus was measured by TCID50 assay with the 10-fold dilution of each sample used for virus titration (Reed and Muench, 1938). In some viruses, the virus protein and genome expression levels were detected by Western blot analysis and real-time qRT-PCR, respectively, as described below. The IC$_{50}$s of the compounds were calculated.

Real-Time qRT-PCR.

The quantity of virus genome in the NV replicon-harboring cells was measured by real-time qRT-PCR with One-step Platinum qRT-PCR kit (Invitrogen, Carlsbad, Calif.), following an established protocol with specific primers and probes as described previously (Chang and George, 2007a). For qRT-PCR, the total RNA in cells (in 6-well plate) was extracted with RNeasy kit (Qiagen, Valencia, Calif.). The primer sequences for NV were: Forward 5'-CGYTGGATGCGITTYCATGA-3' (SEQ ID NO:3) and reverse 5'-CTTAGACGC-CATCATCATTYAC-3' (SEQ ID NO:4). The probe sequence used was: FAM-5'-AGATYGCGITCICCTGTCCA-3'-Iowa Black (SEQ ID NO:5). The qRT-PCR amplification was performed in a SmartCycler (Cepheid, Sunnyvale, Calif.) with the following parameters: 45° C. for 30 min, and 95° C. 10 min, followed by 40 cycles of denaturation at 95° C. for 30 s, annealing at 50° C. for 1 min and elongation at 72° C. for 30 s. For quantity control, qRT-PCR for β-actin was performed as described previously (Spann et al., 2004). The relative genome levels in cells with various treatments were calculated after the RNA levels were normalized with those of β-actin.

Western Blot Analysis. Protein samples of HG23 cells or MNV-1 infected RAW 267.4 cells with various treatments were prepared in SDS-PAGE sample buffer containing 1% β-mercaptoethanol, and sonicated for 20 sec. The proteins were resolved in a 10% Novex Tris-Bis gel (Invitrogen) and transferred to a nitrocellulose membrane. The membranes were probed with guinea pig antibodies specific for NV Pro-Pol protein and the binding of the antibodies was detected with peroxidase-conjugated, goat anti-guinea pig IgG (Sigma-Aldrich). In addition, membranes were probed with rabbit antiserum specific for β-actin and peroxidase-conjugated, goat anti-rabbit IgG as a loading control. Following incubation with a chemiluminescent substrate (SuperSignal West Pico Chemiluminescent Substrate, Pierce Biotechnology, Rockford, Ill.), signals were detected with X-ray film.

Cell Cytotoxicity. The nonspecific cytotoxic effects of each compound on cells were monitored by observation under a microscopy and CytoTox 96 Non-radioactive cytotoxicity assay (Promega, Madison, Wis.).

Example 6

Peptidyl α-Hydroxyphosphonate Inhibitors

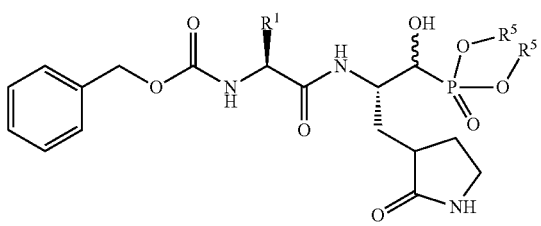

The present Example describes the results of preliminary studies related to the inhibition of norovirus 3CL protease by peptidyl α-hydroxyphosphonates. To our knowledge, this is the first time that α-hydroxyphosphonate transition state mimics have been used in the inhibition of a viral cysteine protease.

The design of α-hydroxyphosphonate inhibitor rested on the following considerations: (A) Previous studies have shown that the α-hydroxyester and α-hydroxyphosphonate moieties function as effective transition state mimics which, when linked to a peptidyl recognition element that is tailored to the substrate specificity of a target protease, yields highly potent inhibitors. This approach has been successfully used in the design of highly effective inhibitors of human renin. (B) NV 3CL protease is a cysteine endoprotease with a chymotrypsin-like fold, a His-Cys-Glu triad, and an extended binding site. Mapping of the active site of 3CL protease using chromogenic and fluorogenic substrates has shown that the protease has a strong preference for a -D/E-F/Y-X-L-Q-G- sequence (See Table 1; SEQ ID NO:6), where X is H, E or Q, and cleavage is at the Q-G ($P_1$-$P_1'$) bond; (C) We have previously demonstrated that the presence of a $P_2$ cyclohexylalanine residue results in a significant enhancement in potency and cellular permeability; (d) based on the aforementioned considerations, it was envisaged that an inhibitor represented by the structure above may display high in vitro inhibitory activity toward NV 3CL protease, as well as anti-norovirus activity in a cell-based replicon system. Described herein are the results of preliminary studies with this α-hydroxyphosphonate inhibitor.

Figure 10:
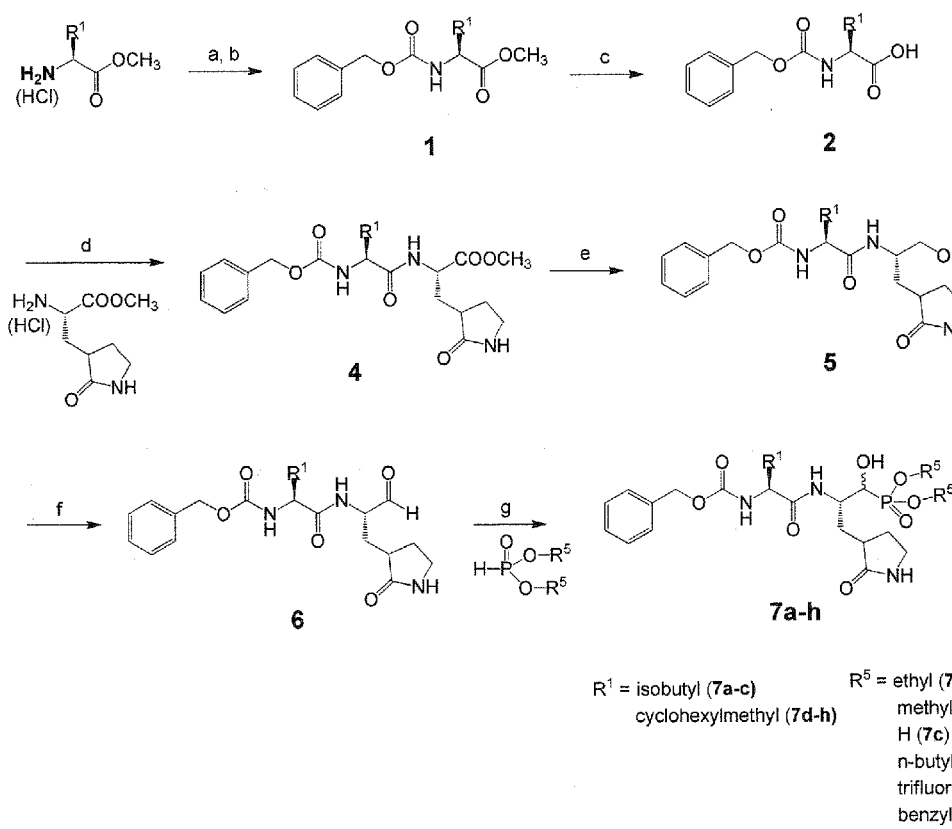
FIG. 10 shows the reaction scheme used to synthesize an α-hydroxyphosphonate in Example 5.

The α-hydroxyphosphonate inhibitor was constructed by transforming commercially available (L) cyclohexyl alanine to the corresponding ester and subsequent conversion of the ester to the isocyanate by refluxing with trichloromethyl chloroformate in dioxane (FIG. 10).

Subsequent reaction with alcohol yielded the N-protected amino acid ester which was hydrolyzed with LiOH/aq THF to yield the corresponding acid, which was then coupled to the methyl ester of a previously-reported $P_1$ glutamine surrogate. The reaction sequence chosen is highly tractable and permits facile modification of the cap by reaction with an array of structurally-diverse alcohols. This is of paramount importance in terms of optimizing pharmacological activity, ADMET, and PK via cap modifications. Reduction of the N-protected amino acid ester with lithium borohydride, followed by oxidation with Dess-Martin periodinane reagent, yielded the corresponding dipeptidyl aldehyde which was reacted with an array of dialkyl phosphites and triethylamine in dichloromethane to yield the desired compounds as mixtures of epimers (listed in Table 4).

TABLE 4

| Compound | $R^1$ | $R^5$ | $IC_{50}$ μM | $EC_{50}$ μM |
|---|---|---|---|---|
| 7a(skm-3-74) | isobutyl | ethyl | >50 | 1.1 |
| 7b(MG-2-48) | isobutyl | methyl | >50 | 3.5 |
| 7c(MG-2-49) | isobutyl | H | >50 | 0.8 |
| 7d(skm-3-73) | cyclohexylmethyl | ethyl | >50 | 0.25 |
| 7e(MG-2-53) | cyclohexylmethyl | methyl | >50 | 2.8 |
| 7f(skm-3-79) | cyclohexylmethyl | n-butyl | >50 | 0.5 |
| 7g(skm-3-77) | cyclohexylmethyl | trifluoroethyl | >50 | 0.25 |
| 7h(skm-3-78) | cyclohexylmethyl | benzyl | >50 | 0.6 |

Substituents shown in FIG. 10.

The inhibitory activity of the generated α-hydroxyphosphonate derivatives was evaluated against norovirus 3CL protease, as well as norovirus in a cell-based replicon system. The selectivity of a representative member of this series of compounds was also assessed using a panel of proteases.

Figure 11:
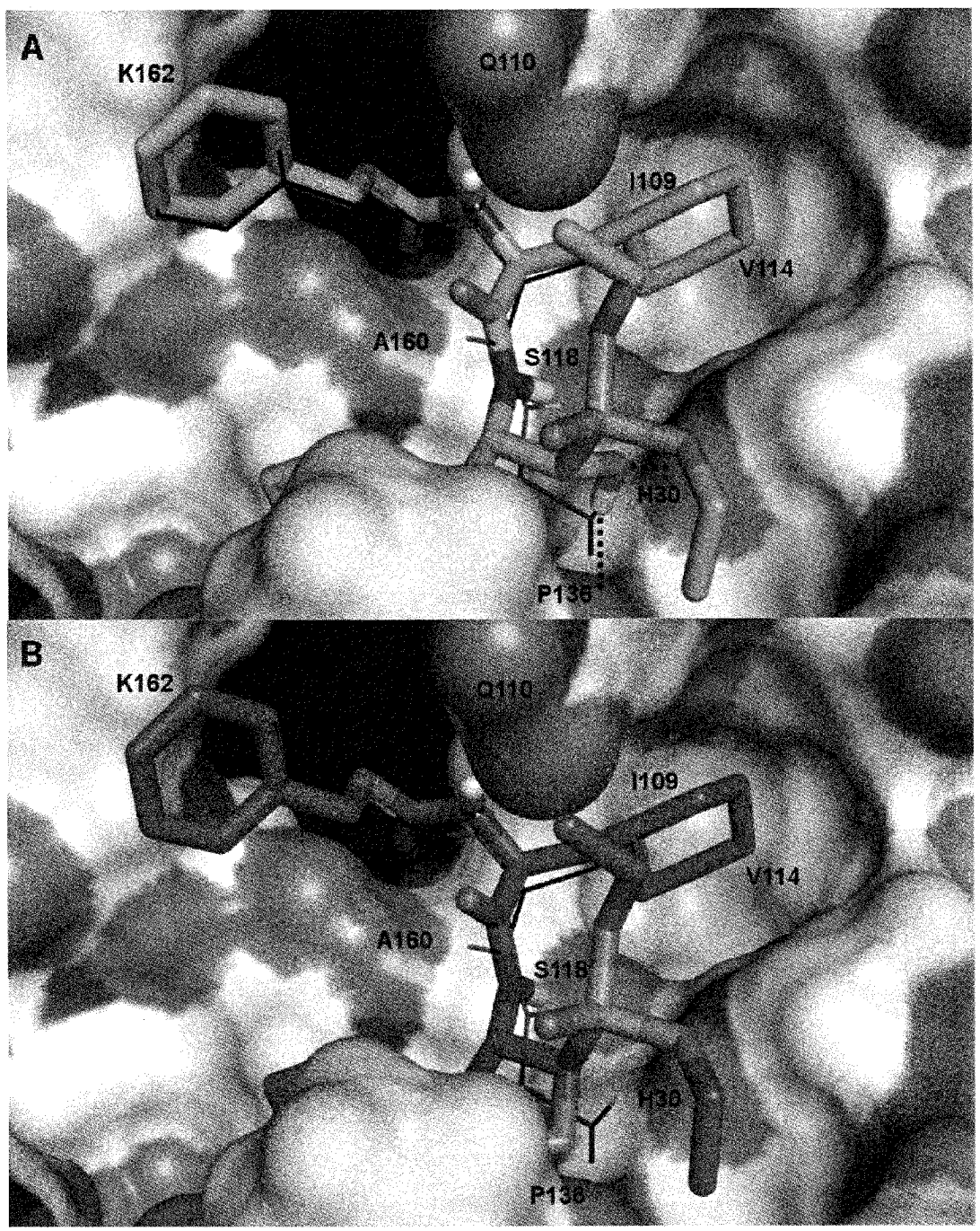
FIG. 11 illustrates the computationally predicted conformers for noncovalent tetrahedral mimics A (CPK colored sticks, with green carbons) and B (CPK sticks; purple carbons) bound to the catalytic site of Norovirus 3CL protease Protein receptors are shown as Connolly surfaces colored as follows: yellow=nonpolar groups; white=weakly polar alkyl and aryl groups; cyan =polar H, blue=polar N and red=polar O. In both cases, the predicted conformer of the corresponding tetrahedral adduct (thin sticks; CPK colors with black carbons) is shown for reference.

In order to gain insight and understanding into the binding of epimers A and B of compound 7a (Table 4), molecular mechanics simulations using the Avogadro program (MMFF94 potentials and electrostatics were used to qualitatively assess the relative affinities of compounds A and B (FIG. 11). To accomplish this, the receptor model was crafted using a recent crystal structure of NV 3CL protease with a bound peptidic ligand by removing water molecules and adding protons (per physiological pH) using the PyMol program. A preliminary model for the bound conformation of the tetrahedral adduct was built within the receptor using Avogadro, as a covalent extension to Cys 139 that mimicked the conformation of the cocrystallized inhibitor from the 2IPH structure and placed the ligand cyclohexyl group in the hydrophobic pocket occupied by the leucyl sidechain of the peptidyl inhibitor. The resulting preliminary model was subjected to 500 steps of molecular mechanics optimization. The structures of A and B were then constructed from the adduct in Avogadro by deleting the covalent attachment to Cys 139, specifying the hydroxyl and the diethyl phosphate groups in a manner commensurate with the stereochemistry of A and B and re-optimizing the resulting structures (again for 500 steps).

The invention claimed is:

1. An antiviral compound comprising:

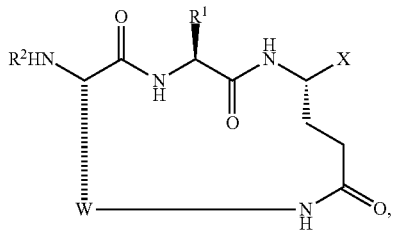
(I)

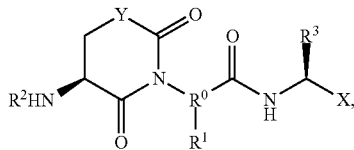
(II)

or the pharmaceutically-acceptable salts thereof, where:

each X is selected from the group consisting of aldehydes; adducts of aldehydes or keytones; ketoamides; α-hydroxyphosphonates; and ketones;

each $R^0$ is —CH— or —N—;

each $R^1$ is a natural or non-naturally occurring amino acid side chain selected from the group consisting of branched or unbranched alkyl, cycloalkyl, aryl, arylalkyl, or a combination thereof;

each $R^2$ is selected from the group consisting of —C(O)OR$^8$, where $R^8$ is alkyl, cycloalkyl, or substituted or unsubstituted: aryl, arylalkyl, aryloxy, heteroaryloxy, arylalkoxy, heteroarylalkoxy, or aromatic heterocyclic ring; —C(O)NHR$^9$, where $R^9$ is alkyl, cycloalkyl, or substituted or unsubstituted: aryl, arylalkyl, aryloxy, heteroaryloxy, arylalkoxy, heteroarylalkoxy, or aromatic heterocyclic ring; and —SO$_2$R$^{10}$, where $R^{10}$ is alkyl, cycloalkyl, or substituted or unsubstituted: aryl, arylalkyl, aryloxy, heteroaryloxy, arylalkoxy, heteroarylalkoxy, or aromatic heterocyclic ring;

each $R^3$ is selected from the group consisting of

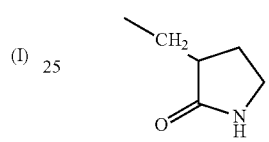

and —(CH$_2$)$_2$C(O)NR$^{14}$R$^{15}$, where $R^{14}$ is alkyl, cycloalkyl, or arylalkyl, and $R^{15}$ is H or alkyl, or $R^{14}$ and $R^{15}$ are tethered together to form a cyclic amine;

each W is selected from the group consisting of —(CH$_2$)$_x$—, where x is 4 to 10; —CH$_2$Q (CH$_2$)$_z$—, where Q is S or O, and z is 4 to 8; —(CH$_2$)$_m$C(O)NR$^{11}$(CH$_2$)$_p$—, where $R^{11}$ is H or methyl, m is 1 to 2, and p is 3 to 6; —CH$_2$Im(CH$_2$)$_r$—, where Im is imidazole and r is 3 to 6; —(CH$_2$)$_s$Tr(CH$_2$)$_s$—, where Tr is a 1,4— or 1,5-substituted triazole and each s is 1 to 4; and —(CH$_2$)$_t$R$^{12}$(CH$_2$)$_t$-, where $R^{12}$ is a phenyl or heterocyclic ring, and each t is 1 to 4; and each Y is —CH$_2$— or NR$^{13}$, where $R^{13}$ is H, alkyl, cycloalkyl, or arylalkyl.

2. The compound of claim 1, wherein said compound inhibits viral replication of one or more viruses selected from the group consisting of caliciviruses, picornaviruses, and coronaviruses.

3. The compound of claim 2, wherein said compound inhibits 3C or 3C—like protease activity of said virus.

4. The compound of claim 1, wherein said compound has broad spectrum activity effective against multiple viruses.

5. The compound of claim 1, wherein X is selected from the group consisting of:
an aldehyde of the formula —CHO;
a ketoamide of the formula
—C(O)C(O)NHR$^4$,
where $R^4$ is a branched or unbranched alkyl, cycloalkyl, or arylalkyl; and
an α-hydroxyphosphonate of the formula
—CH(OH)(P=O)(OR$^5$)$_2$,
where each $R^5$ is —H, a substituted or unsubstituted alkyl, aryl, or arylalkyl.

6. The compound of claim 1, wherein said compound is a macrocycle according to formula 1, and wherein $R^1$ is isobutyl, cyclohexylalkyl, or benzyl.

7. The compound of claim 1, wherein said compound is a peptidomimietic according to formula II, and wherein $R^1$ is alkyl, cycloalkyl, or arylalkyl.

8. The compound of claim 1, wherein said compound is a peptidomimetic according to formula II, and wherein each $R^3$ is
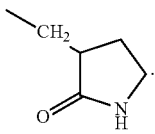
9. The compound of claim 1, wherein each $R^2$ is substituted or unsubstituted carboxybenzyl.
10. The compound of claim 1, wherein said compound is selected from the group consisting of:
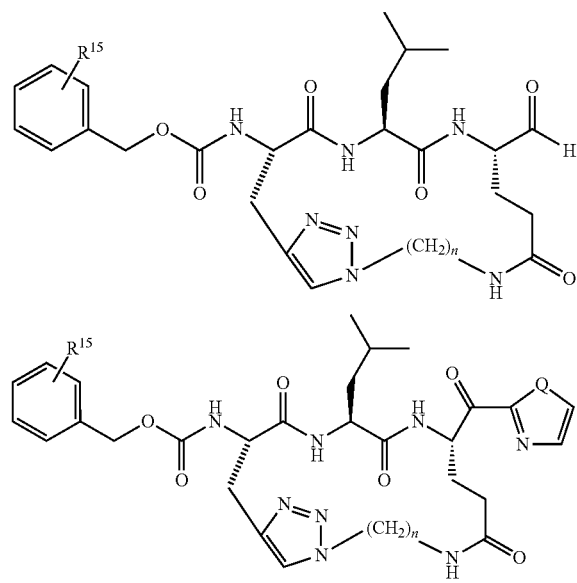
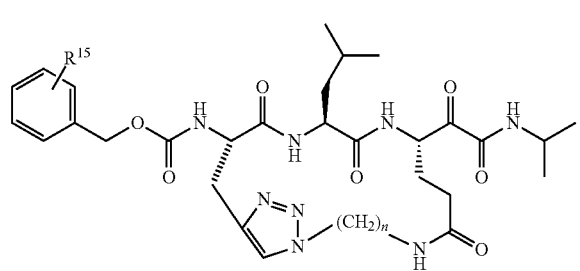
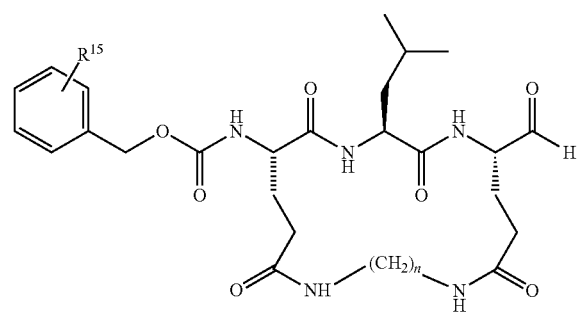
-continued
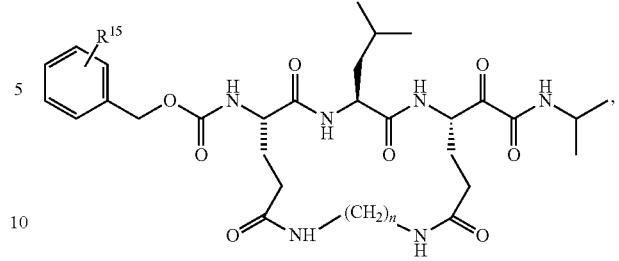
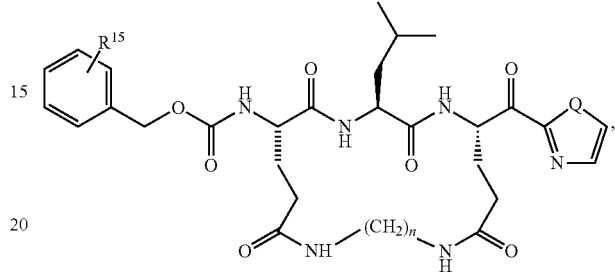
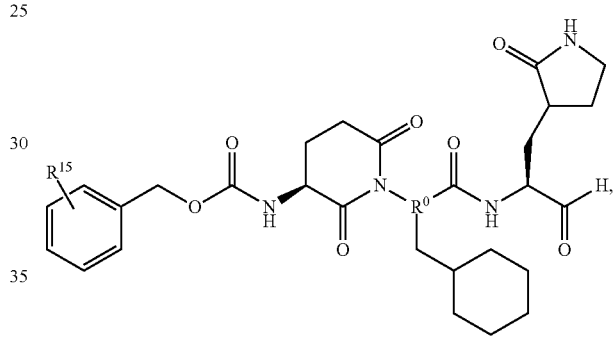
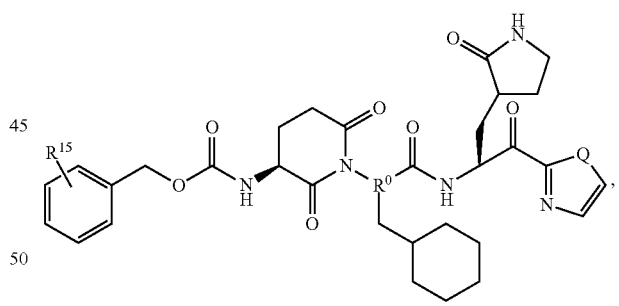
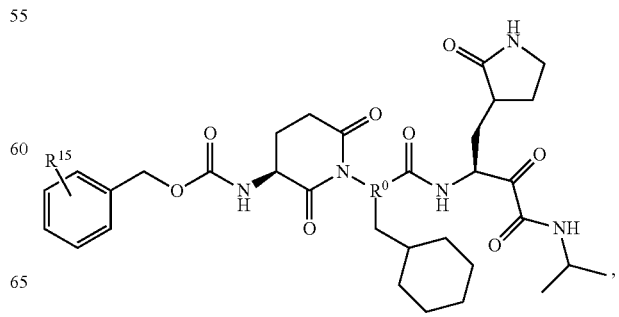

37
-continued
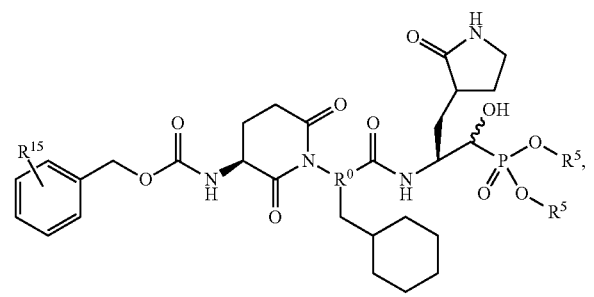
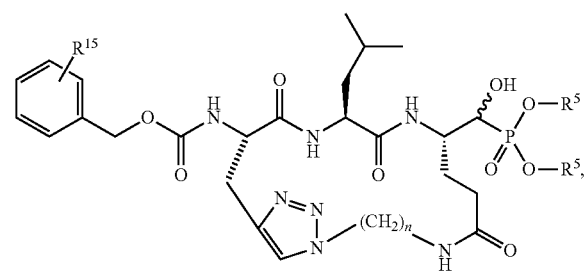
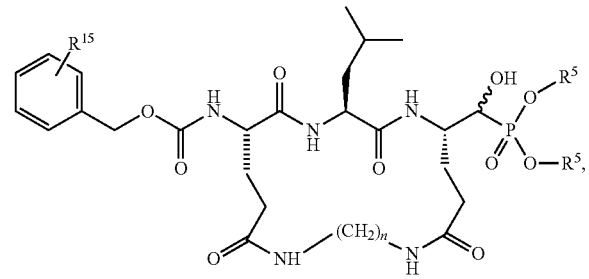
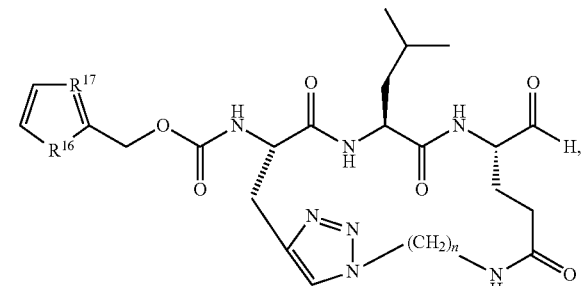
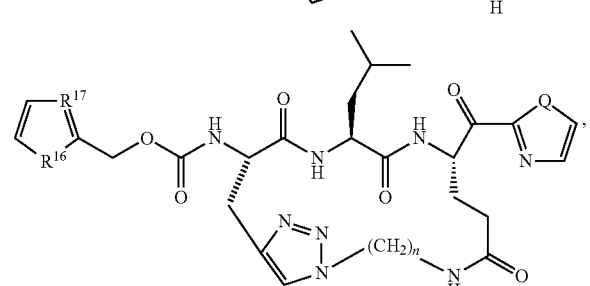
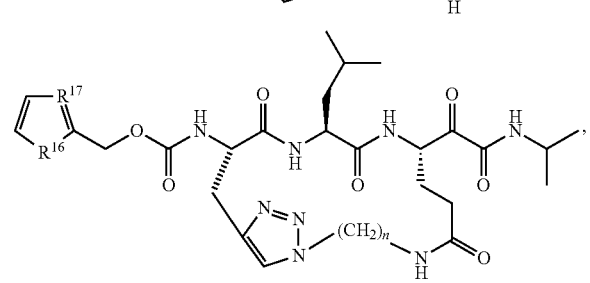
38
-continued
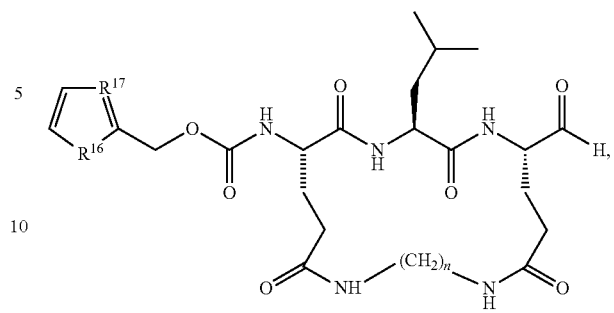
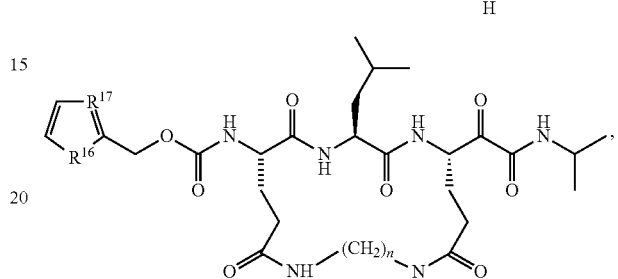
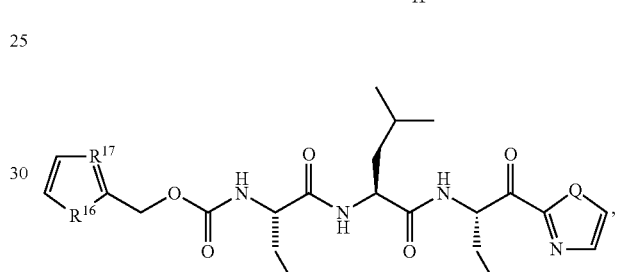
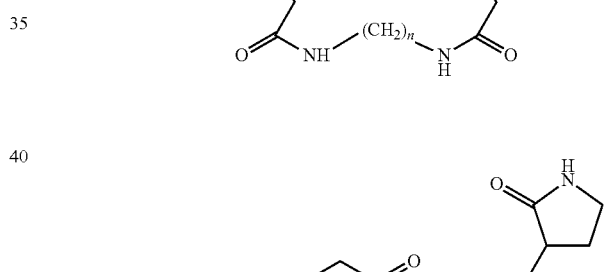
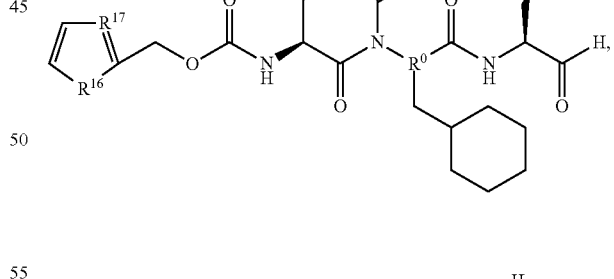
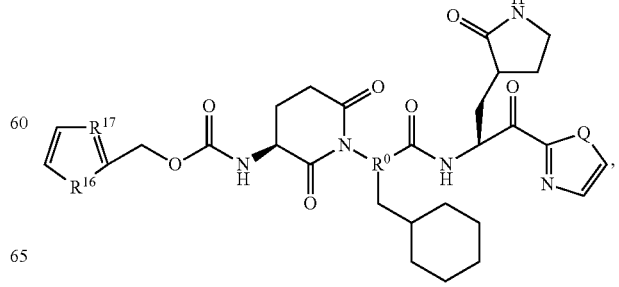

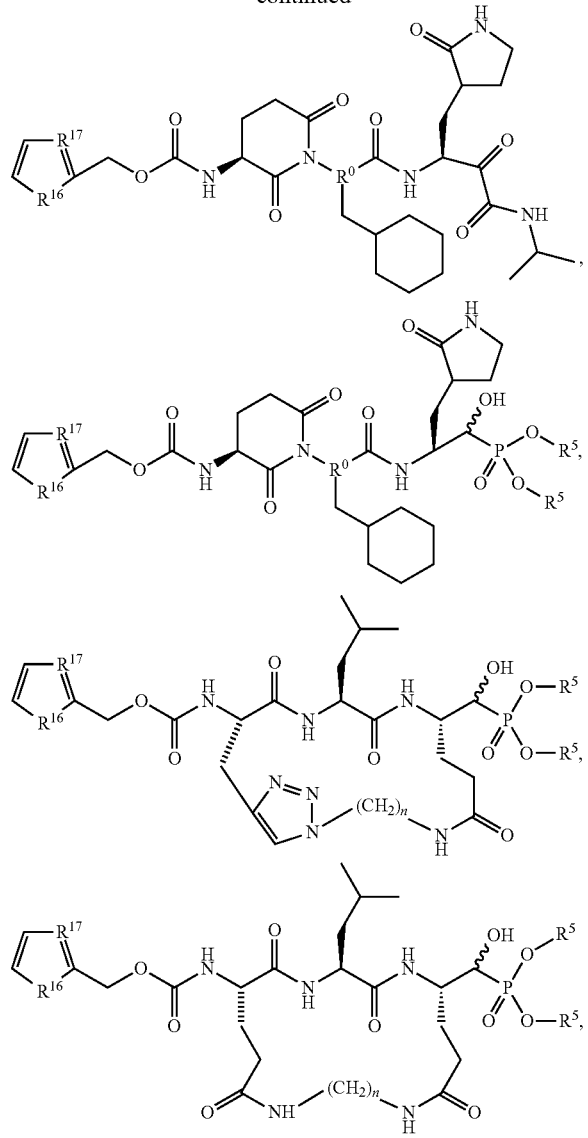

and the pharmaceutically-acceptable salts thereof, where:
- each n is 1, 2, 3, or 4;
- each Q is O or S;
- each $R^0$ is CH or N;
- each $R^5$ is H, methyl, ethyl, n-butyl, trifluoroethyl, or benzyl;
- each $R^{15}$ is hydrogen, halogen, cyano, methoxy, thioether, sulfone, amino, or hydroxyl;
- each $R^{16}$ is NH, O, or S; and
- each $R^{17}$ is CH or NH.

11. A method of treating a viral infection from one or more viruses selected from one or more viruses selected from the group consisting of caliciviruses, picornaviruses, and/or coronaviruses in a subject, said method comprising administering to said subject a therapeutically-effective amount of a first antiviral compound according to claim 1.

12. The method of claim 11, wherein said compound has a therapeutic index of greater than about 50:1.

13. The method of claim 11, wherein said compound is dispersed in a pharmaceutically-acceptable carrier.

14. The method of claim 13, further comprising providing a unit dosage form of said compound dispersed in said pharmaceutically-acceptable carrier prior to said administering.

15. The method of claim 11, further comprising administering a second antiviral compound to said subject.

16. The method of claim 15, wherein said second antiviral compound is an antiviral compound according to claim 1, said first antiviral compound being different from said second antiviral compound.

17. The method of claim 15, wherein said first and second antiviral compounds are co-administered.

18. The method of claim 15, both of said compounds being dispersed or dissolved together in a pharmaceutically-acceptable carrier.

19. The method of claim 11, wherein said virus is selected from the group consisting of human norovirus, human sapovirus, Norwalk virus, feline calicivirus, MD145, murine norovirus, vesicular exanthema of swine virus, rabbit hemorrhagic disease virus, human enterovirus, enterovirus 71, poliovirus, coxsackievirus, foot-and-mouth disease virus, hepatitis A, porcine teschovirus, rhinovirus, human coronavirus, transmissible gastroenteritis virus, murine hepatitis virus, bovine coronavirus, feline infectious peritonitis virus, and severe acute respiratory syndrome coronavirus.

20. The method of claim 11, wherein said subject is suffering from a viral infection from a calicivirus, picornavirus, and/or coronavirus prior to said administering.

21. The method of claim 11, wherein said treatment comprises prophylactic administration.

22. A broad spectrum antiviral composition comprising a first antiviral compound according claim 1 dispersed in a pharmaceutically-acceptable carrier.

23. The composition of claim 22, wherein said carrier is selected from the group consisting of sterile isotonic aqueous buffer, normal saline, phosphate buffered saline, DMSO, sterile water, oil-in-water emulsion, water-in-oil emulsion, and mixtures thereof.

24. The composition of claim 22, further comprising a second antiviral compound, both of said antiviral compounds being dispersed together in said pharmaceutically-acceptable carrier.

25. The composition of claim 24, wherein said second antiviral compound is an antiviral compound according to claim 1, said first antiviral compound being different from said second compound.

26. A method of preventing or inhibiting replication of a virus in a cell, said method comprising contacting said cell with an antiviral compound according to claim 1, wherein said virus is selected from the group consisting of caliciviruses, picornaviruses, coronaviruses, and combinations thereof.

\* \* \* \* \*

SEQUENCE LISTING

<160> NUMBER OF SEQ ID NOS: 6

<210> SEQ ID NO 1
<211> LENGTH: 7
<212> TYPE: PRT
<213> ORGANISM: Artificial Sequence
<220> FEATURE:
<223> OTHER INFORMATION: Synthetic substrate

<400> SEQUENCE: 1

Asp Phe His Leu Gln Gly Pro
1               5

<210> SEQ ID NO 2
<211> LENGTH: 14
<212> TYPE: PRT
<213> ORGANISM: Artificial Sequence
<220> FEATURE:
<223> OTHER INFORMATION: Synthetic substrate

<400> SEQUENCE: 2

Lys Thr Ser Ala Val Leu Gln Ser Gly Phe Arg Lys Met Glu
1               5                   10

<210> SEQ ID NO 3
<211> LENGTH: 20
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (12)..(12)
<223> OTHER INFORMATION: n is any base or inosine

<400> SEQUENCE: 3
cgytggatgc gnttycatga                                          20

<210> SEQ ID NO 4
<211> LENGTH: 22
<212> TYPE: DNA
<213> ORGANISM: Artificial Sequence
<220> FEATURE:
<223> OTHER INFORMATION: PCR primer

<400> SEQUENCE: 4
cttagacgcc atcatcatty ac                                       22

<210> SEQ ID NO 5
<211> LENGTH: 20
<212> TYPE: DNA
<213> ORGANISM: Artificial Sequence
<220> FEATURE:
<223> OTHER INFORMATION: PCR probe
<220> FEATURE:
<221> NAME/KEY: misc_feature
<222> LOCATION: (9)..(9)
<223> OTHER INFORMATION: n is a or inosine
<220> FEATURE:
<221> NAME/KEY: misc_feature
<222> LOCATION: (12)..(12)
<223> OTHER INFORMATION: n is c, t, or inosine

<400> SEQUENCE: 5
agatygcgnt cncctgtcca                                          20

<210> SEQ ID NO 6
<211> LENGTH: 6

```
<212> TYPE: PRT
<213> ORGANISM: Norovirus
<220> FEATURE:
<221> NAME/KEY: MISC_FEATURE
<222> LOCATION: (1)..(1)
<223> OTHER INFORMATION: Xaa is Asp or Glu
<220> FEATURE:
<221> NAME/KEY: MISC_FEATURE
<222> LOCATION: (2)..(2)
<223> OTHER INFORMATION: Xaa is Phe or Tyr
<220> FEATURE:
<221> NAME/KEY: MISC_FEATURE
<222> LOCATION: (3)..(3)
<223> OTHER INFORMATION: Xaa is His, Glu, or Gln

<400> SEQUENCE: 6

Xaa Xaa Xaa Leu Gln Gly
1               5
```